(12) United States Patent
Kircher et al.

(10) Patent No.: US 9,833,144 B2
(45) Date of Patent: Dec. 5, 2017

(54) PROBES, METHODS OF MAKING PROBES, AND METHODS OF USE

(75) Inventors: Moritz F. Kircher, New York, NY (US); Adam de la Zerda, Woodside, CA (US); Jesse Jokerst, San Francisco, CA (US); Cristina Zavaleta, Palo Alto, CA (US); Sanjiv S. Gambhir, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 702 days.

(21) Appl. No.: 13/344,827

(22) Filed: Jan. 6, 2012

(65) Prior Publication Data

US 2012/0179029 A1 Jul. 12, 2012

Related U.S. Application Data

(60) Provisional application No. 61/430,776, filed on Jan. 7, 2011.

(51) Int. Cl.
| | |
|---|---|
| *A61B 5/05* | (2006.01) |
| *A61B 5/00* | (2006.01) |
| *A61B 34/10* | (2016.01) |
| *A61K 51/12* | (2006.01) |
| *G01R 33/48* | (2006.01) |
| *A61B 90/00* | (2016.01) |

(52) U.S. Cl.
CPC .......... *A61B 5/0042* (2013.01); *A61B 5/0035* (2013.01); *A61B 34/10* (2016.02); *A61B 5/0075* (2013.01); *A61B 5/0095* (2013.01); *A61B 2090/374* (2016.02); *A61B 2090/378* (2016.02); *A61K 51/122* (2013.01); *G01R 33/4808* (2013.01)

(58) Field of Classification Search
None
See application file for complete search history.

(56) References Cited

U.S. PATENT DOCUMENTS

| | | | |
|---|---|---|---|
| 8,194,246 B2 | 6/2012 | Thundat et al. | |
| 2005/0191665 A1* | 9/2005 | Su ................... | G01N 33/54346 435/6.11 |
| 2010/0166650 A1* | 7/2010 | Gambhir ...................... | 424/1.11 |
| 2010/0197937 A1 | 8/2010 | Minami et al. | |

(Continued)

FOREIGN PATENT DOCUMENTS

| | | | |
|---|---|---|---|
| WO | WO 2010/111066 | * | 3/2010 |
| WO | WO 2010/096828 | * | 8/2010 |

OTHER PUBLICATIONS

Rieter et al., "Hybrid Silica Nanoparticles for Multimodal Imaging", 2007, vol. 46, pp. 3680-3682.*

(Continued)

*Primary Examiner* — Christopher Cook
(74) *Attorney, Agent, or Firm* — Thomas | Horstemeyer, LLP

(57) ABSTRACT

Embodiments of the present disclosure provide for probes, methods of using the probe, methods of making the probe, method of imaging a condition (e.g., pre-cancerous tissue, cancer, or a tumor), methods of planning resection of a brain tumor, methods of imaging a brain tumor, and the like.

24 Claims, 21 Drawing Sheets
(18 of 21 Drawing Sheet(s) Filed in Color)

(56) References Cited

U.S. PATENT DOCUMENTS

2011/0282181 A1 11/2011 Wang et al.
2012/0136241 A1 5/2012 Chen et al.

OTHER PUBLICATIONS

Sharma et al., "Gold-Speckled Multimodal Nanoparticles for Noninvasive Bioimaging", Chem. Mater., Sep. 12, 2008, pp. 6087-6094.*
Cho et al., "Inorganic nanoparticle-based contrast agents for molecular imaging", Trends in Molecular Medicine, Dec. 2010, vol. 16, No. 12, pp. 561-573.*
Paeng et al., "Multimodal Molecular Imaging in Vivo", The Open Nuclear Medicine Journal, 2010, 2, pp. 145-152.*
Morawski et al. "Targeted Nanoparticles for Quantitative Imaging of Sparse Molecular Epitopes with MRI", 2004, Magnetic Resonance in Medicine, 51, pp. 480-486.*
Gerion et al., "Paramagnetic Silica-Coated Nanocrystals as an Advanced MRI Contrast Agent", J. Phys. Chem. C 2007, 111, pp. 12542-12551.*
Kircher et al., A Multimodal Nanoparticle for Preoperative Magnetic Resonance Imaging and Intraoperative Optical Brain Tumor Delineation, Cancer Research, 63, Dec. 1, 2003.*

\* cited by examiner

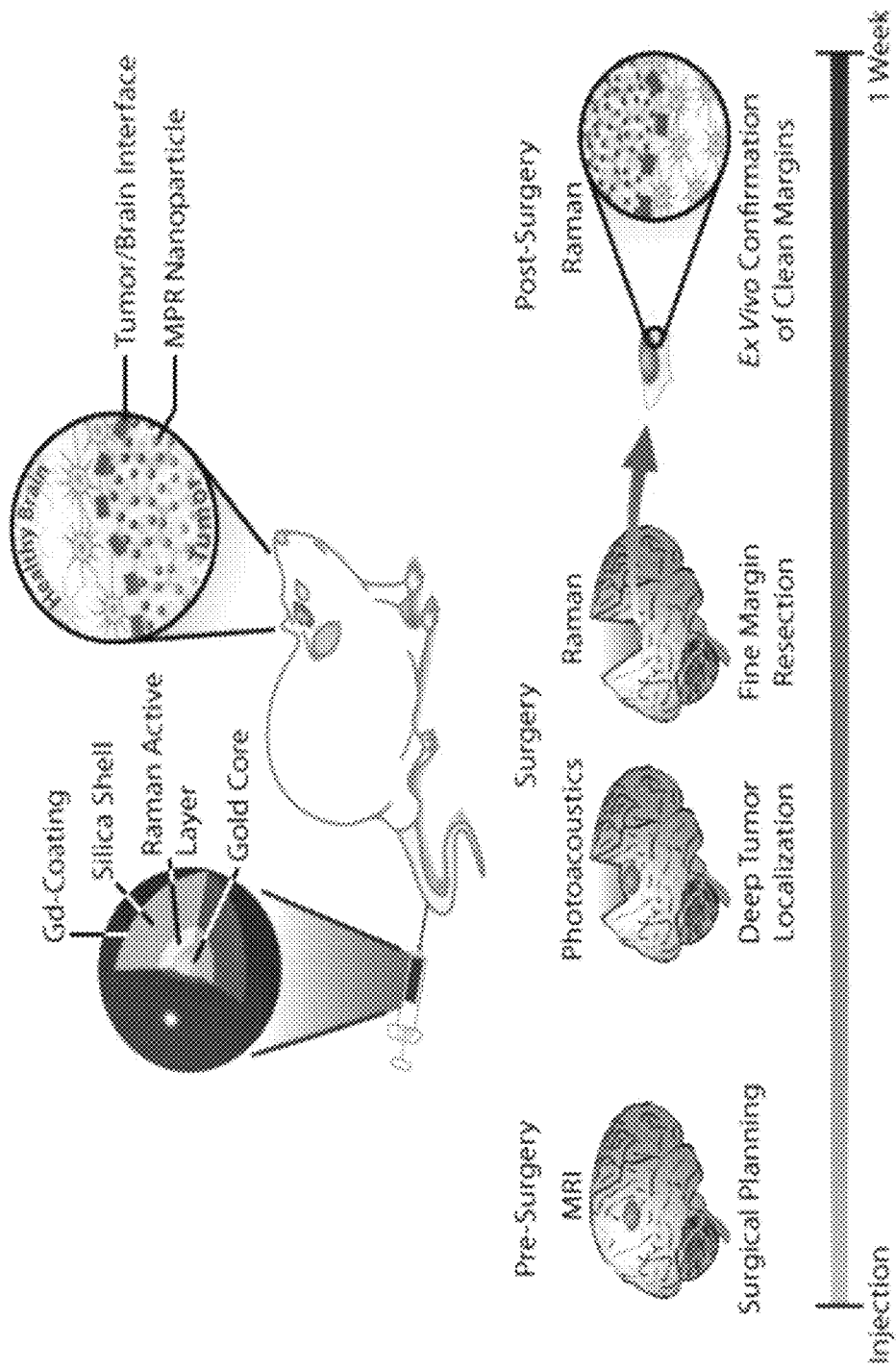
FIG. 1.1

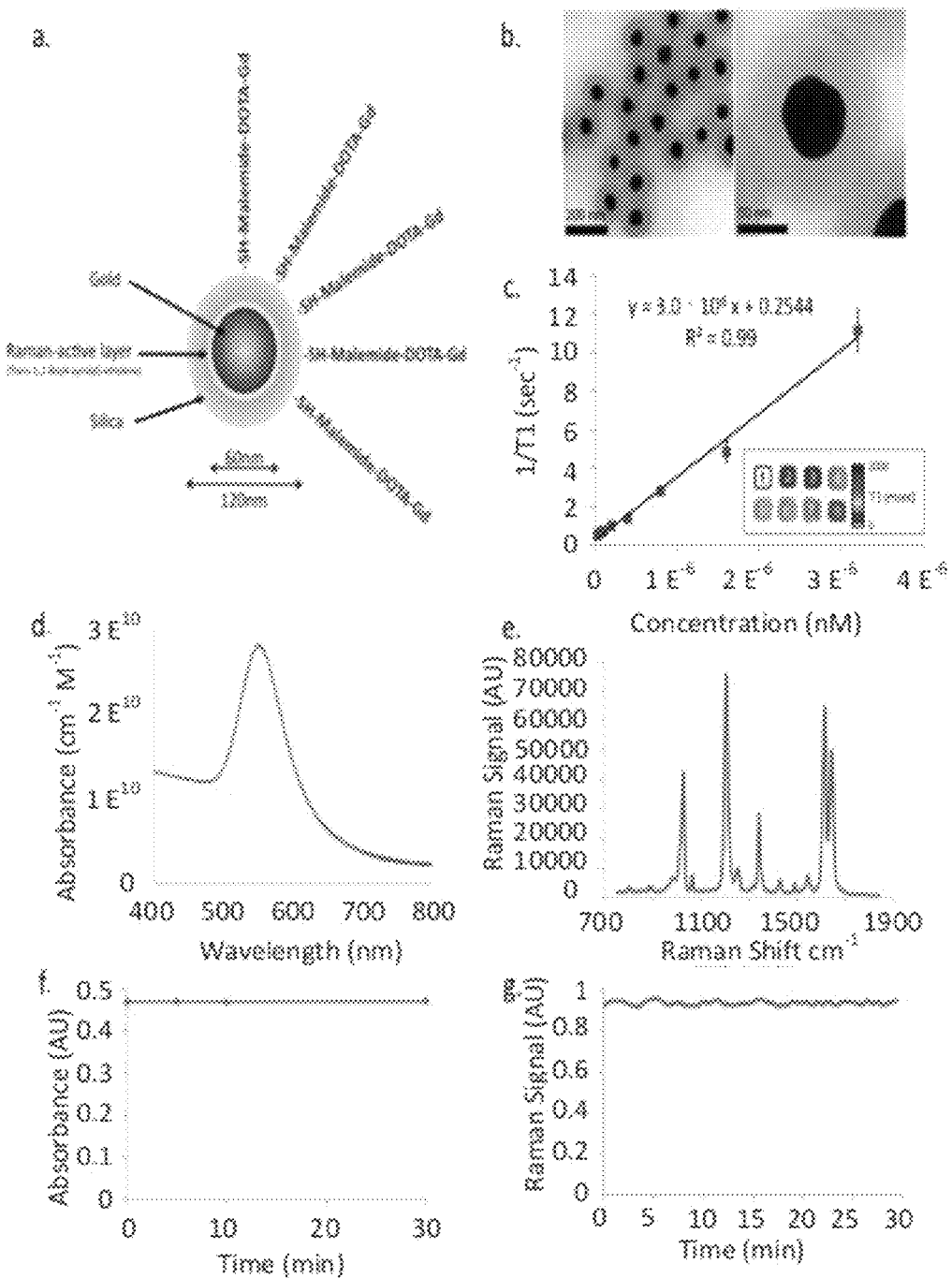
FIG. 1.2

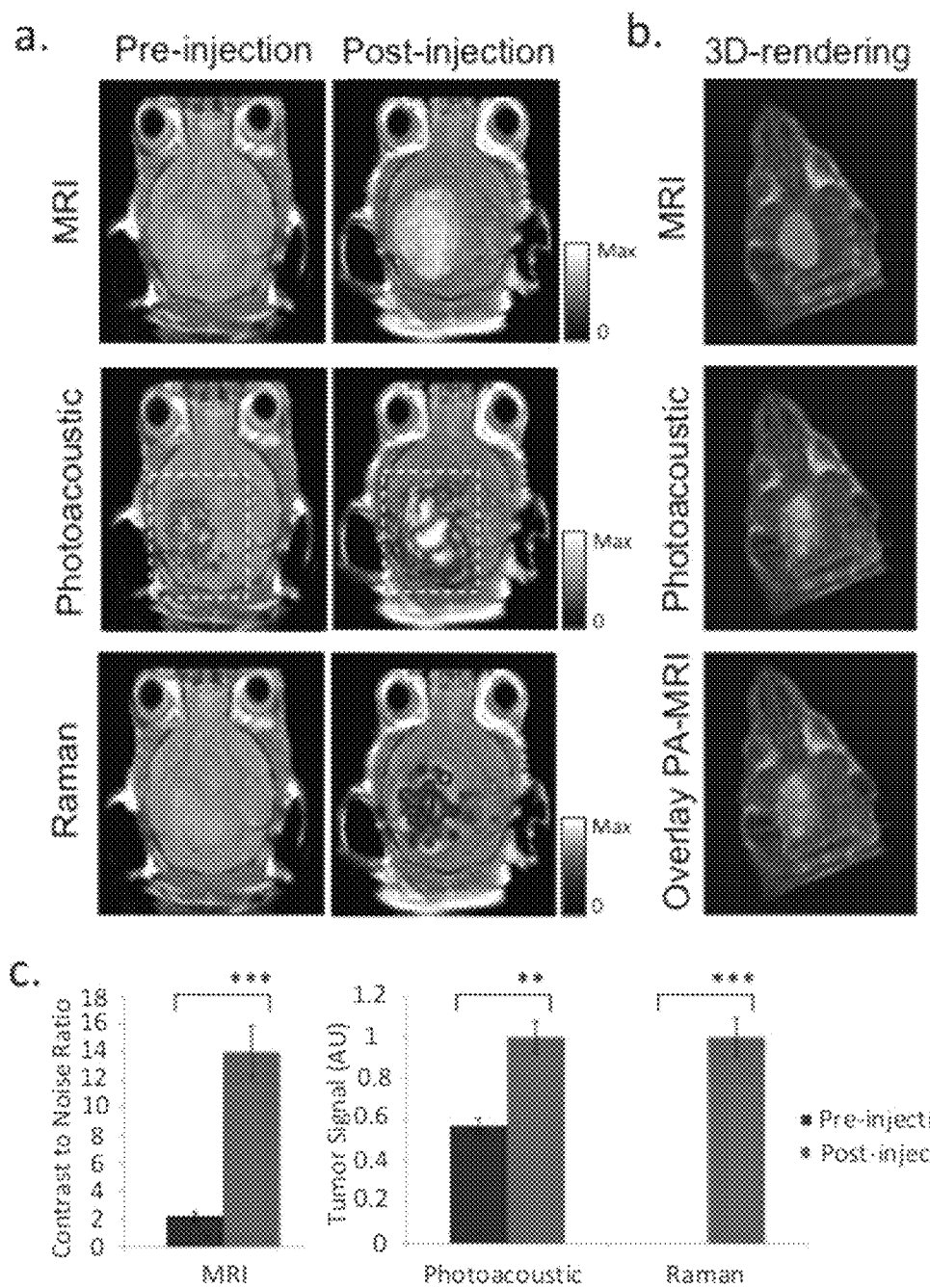
FIG. 1.3

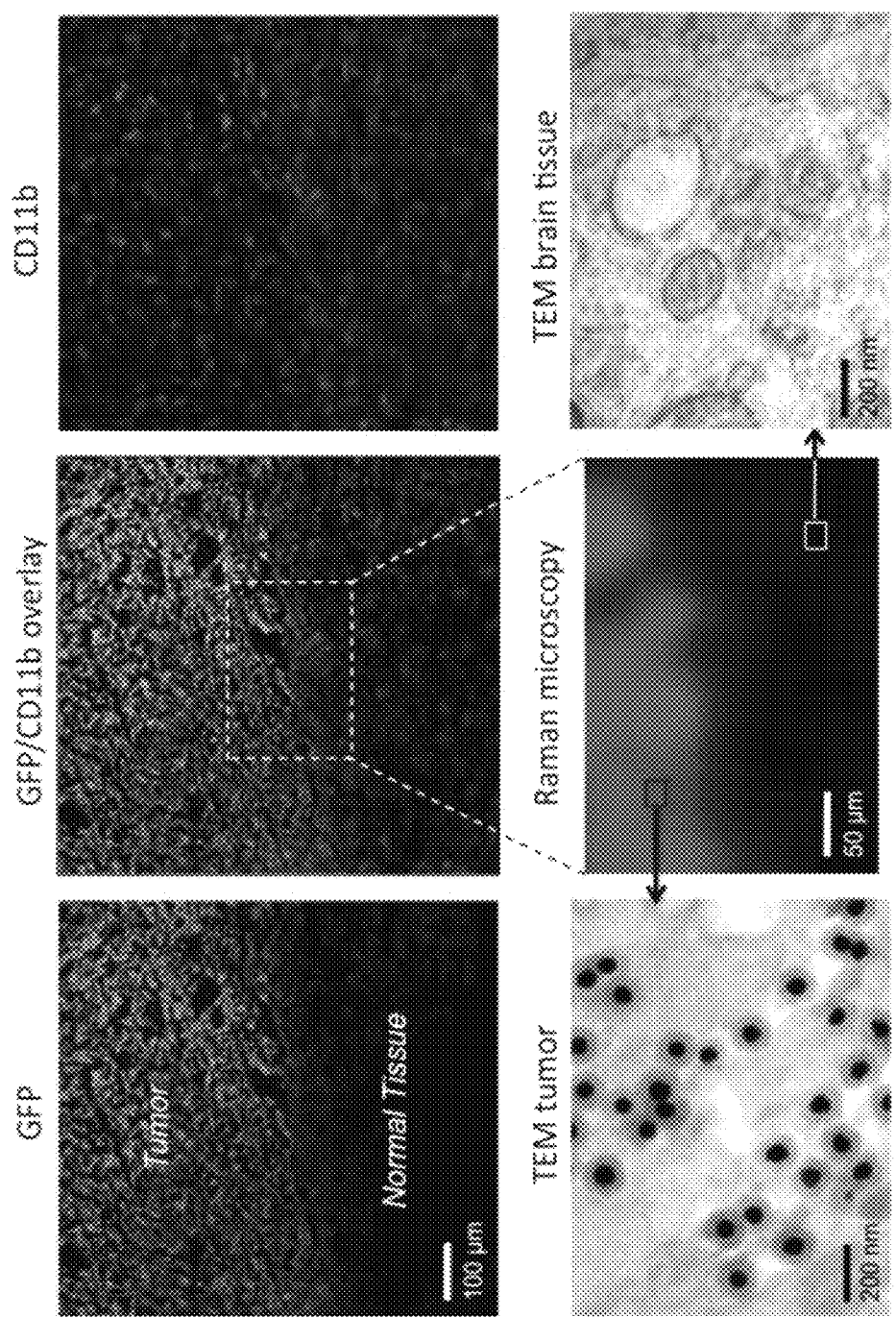
FIG. 1.4

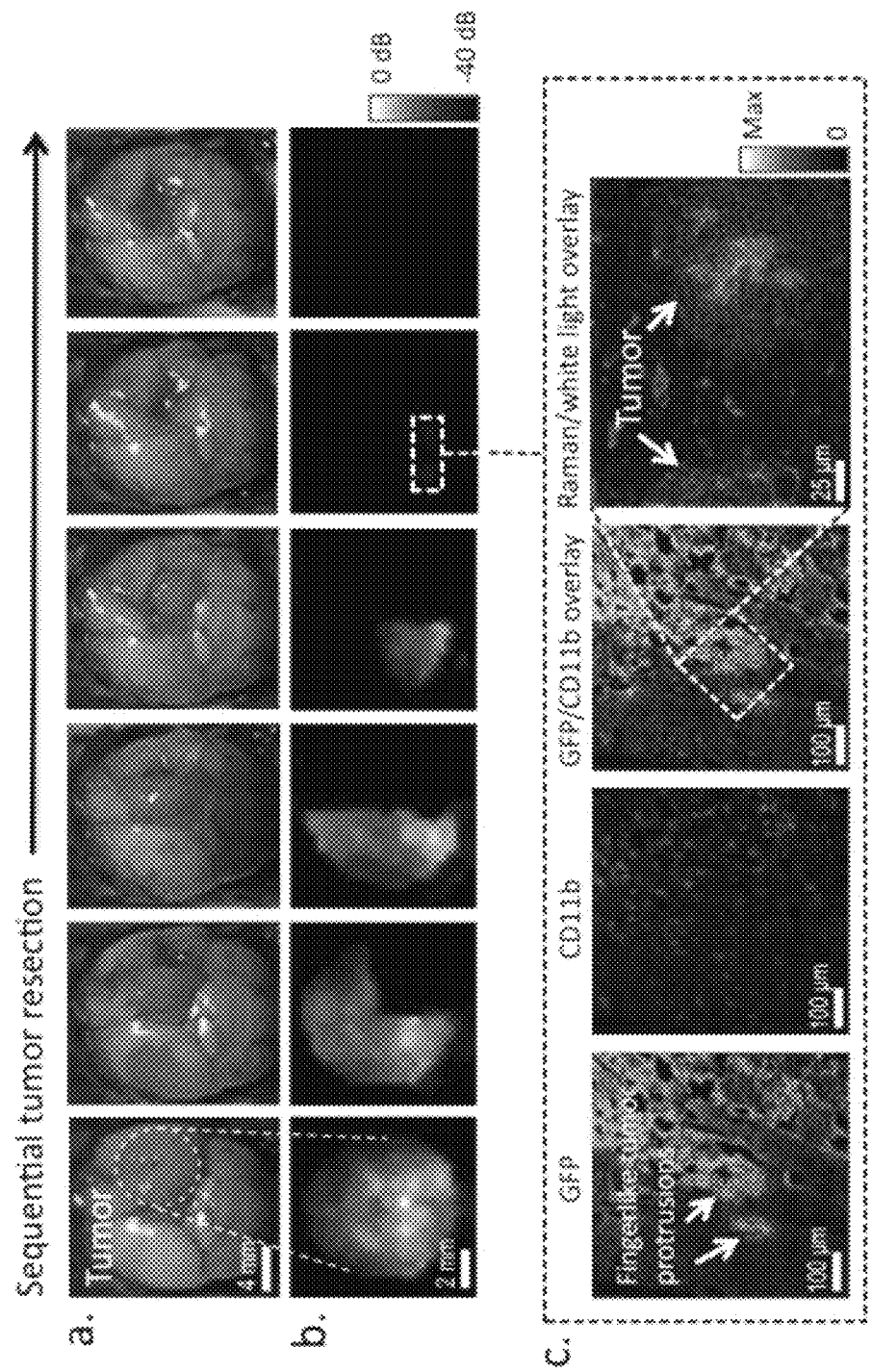
FIG. 1.5

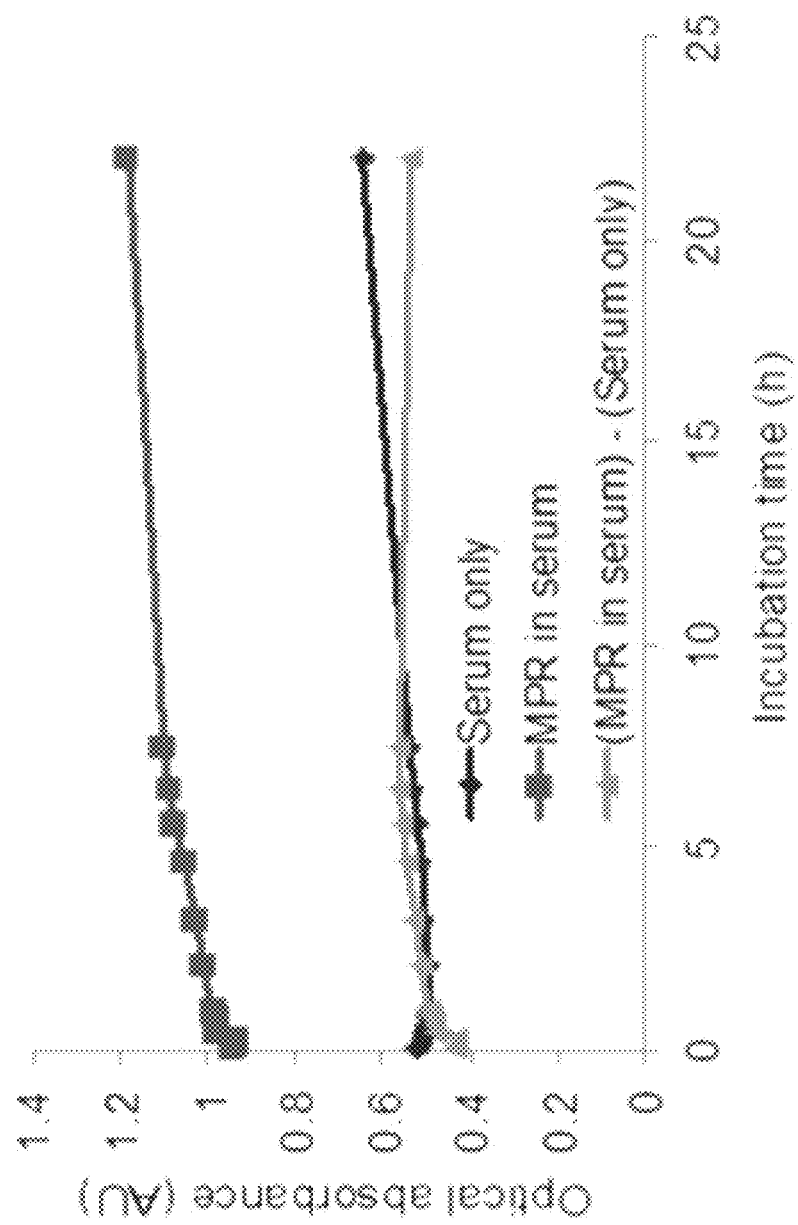
FIG. 1.6

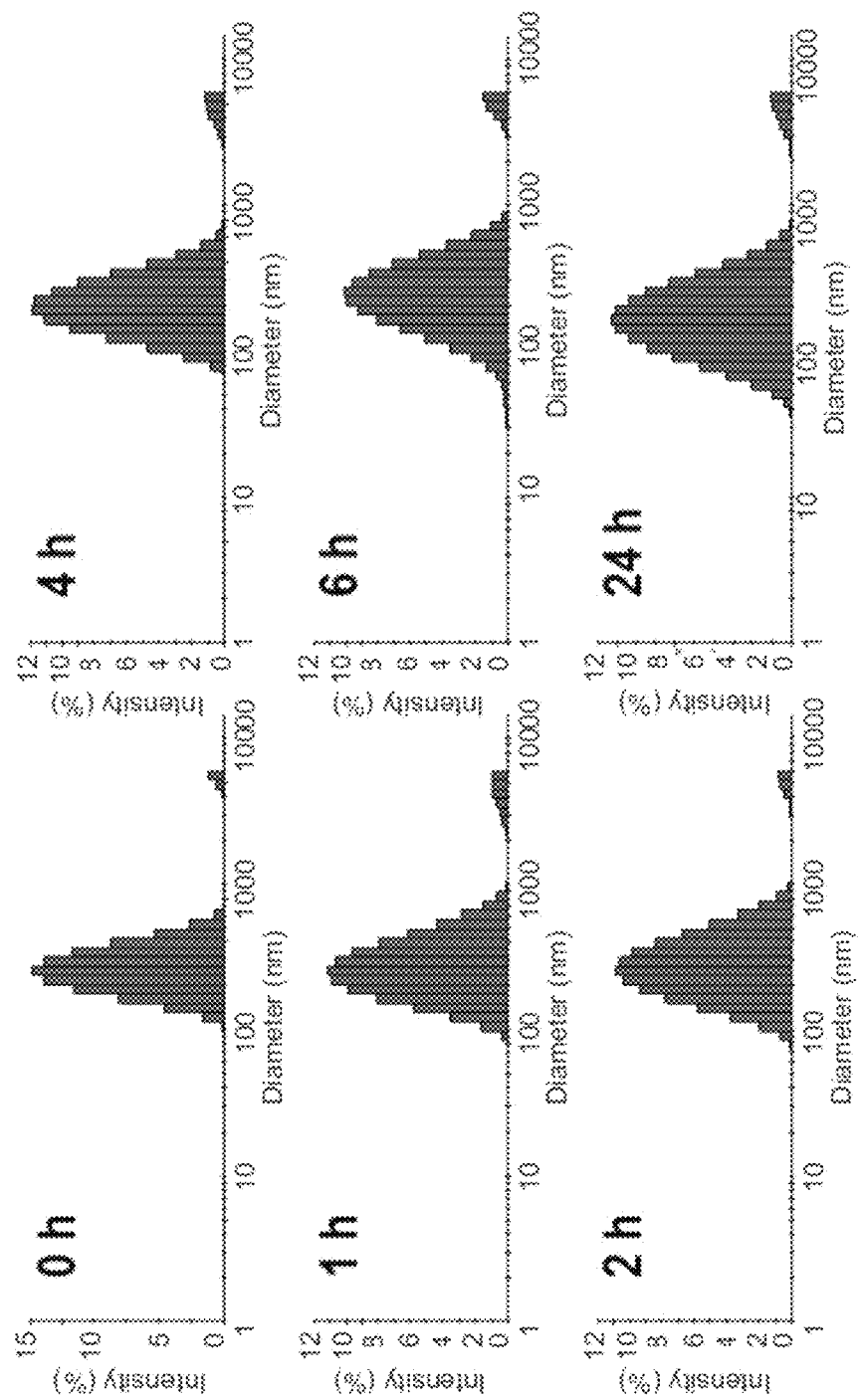
FIG. 1.7

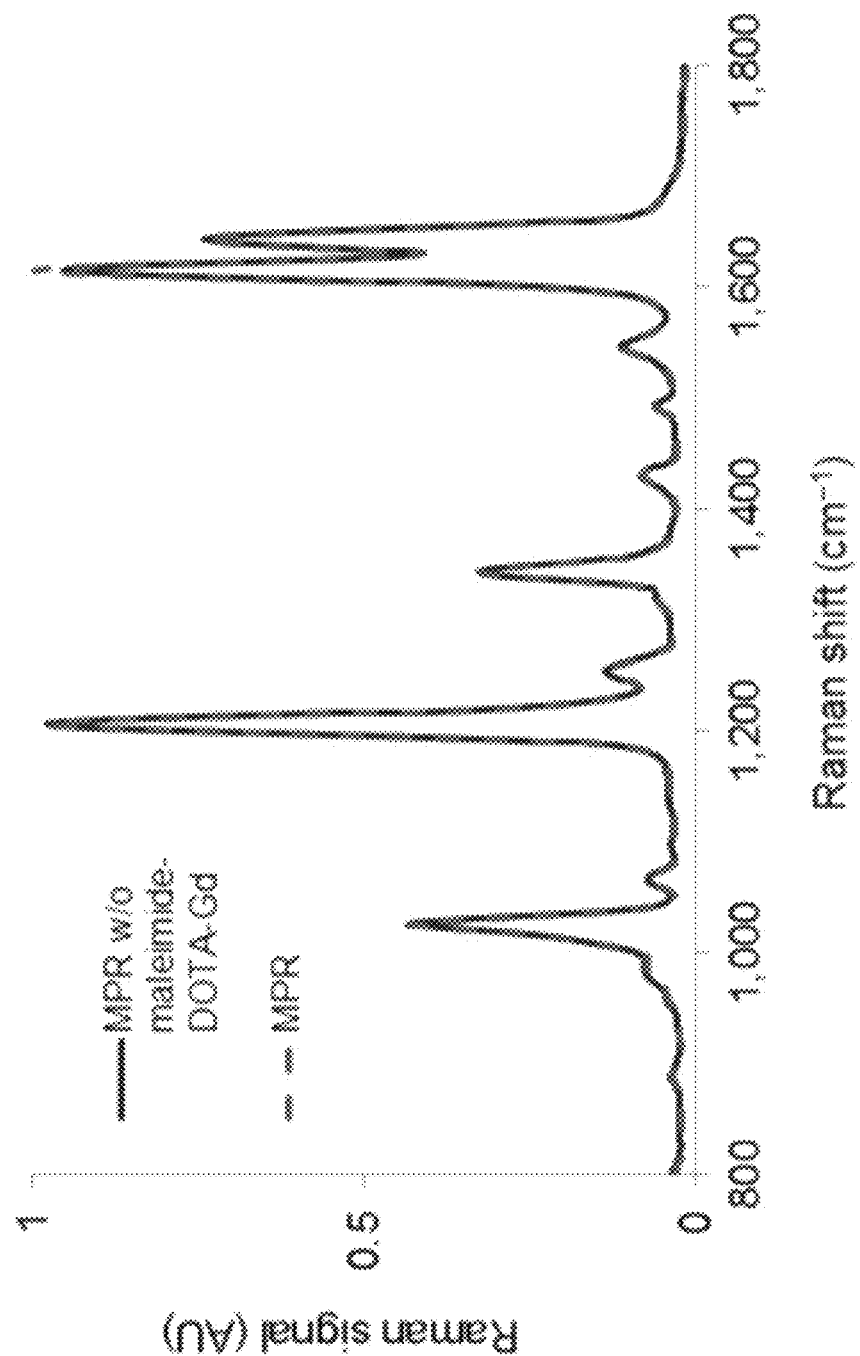
FIG. 1.8

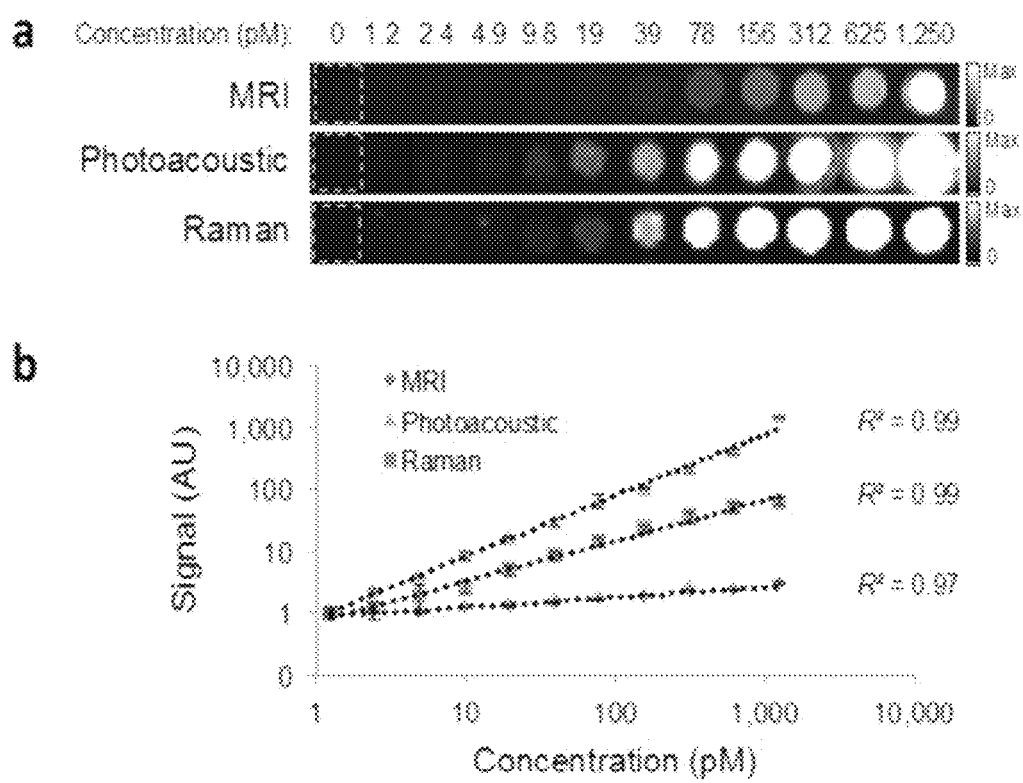
FIG. 1.9
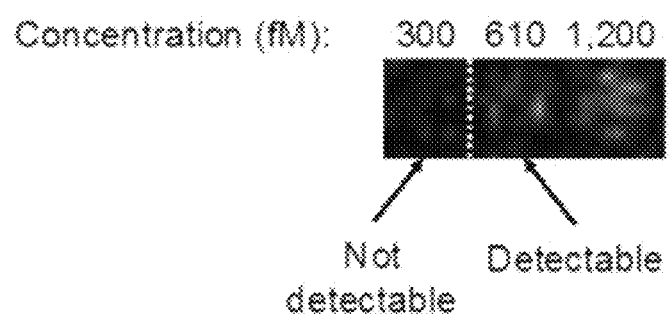
FIG. 1.10

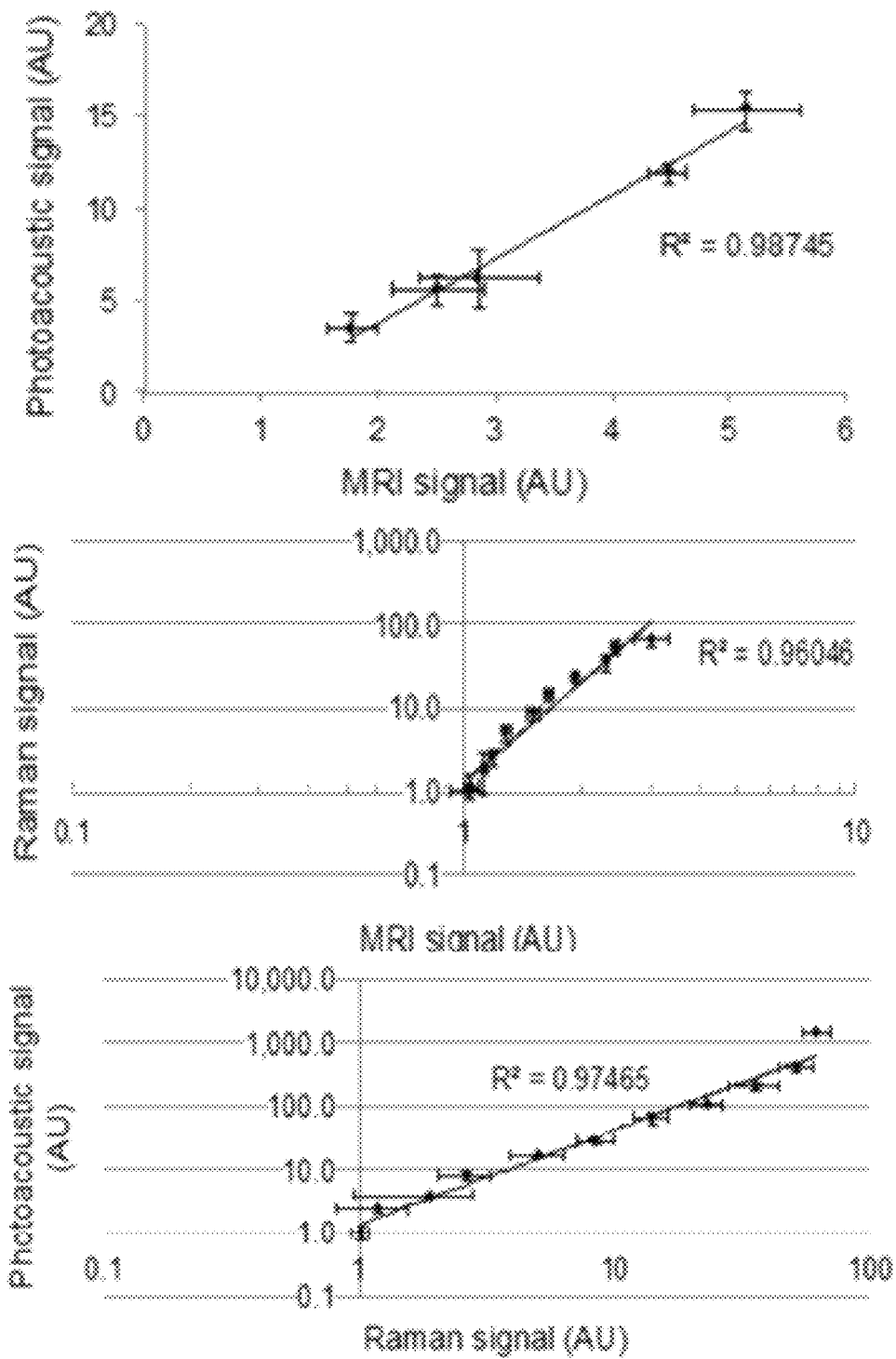
FIG. 1.11

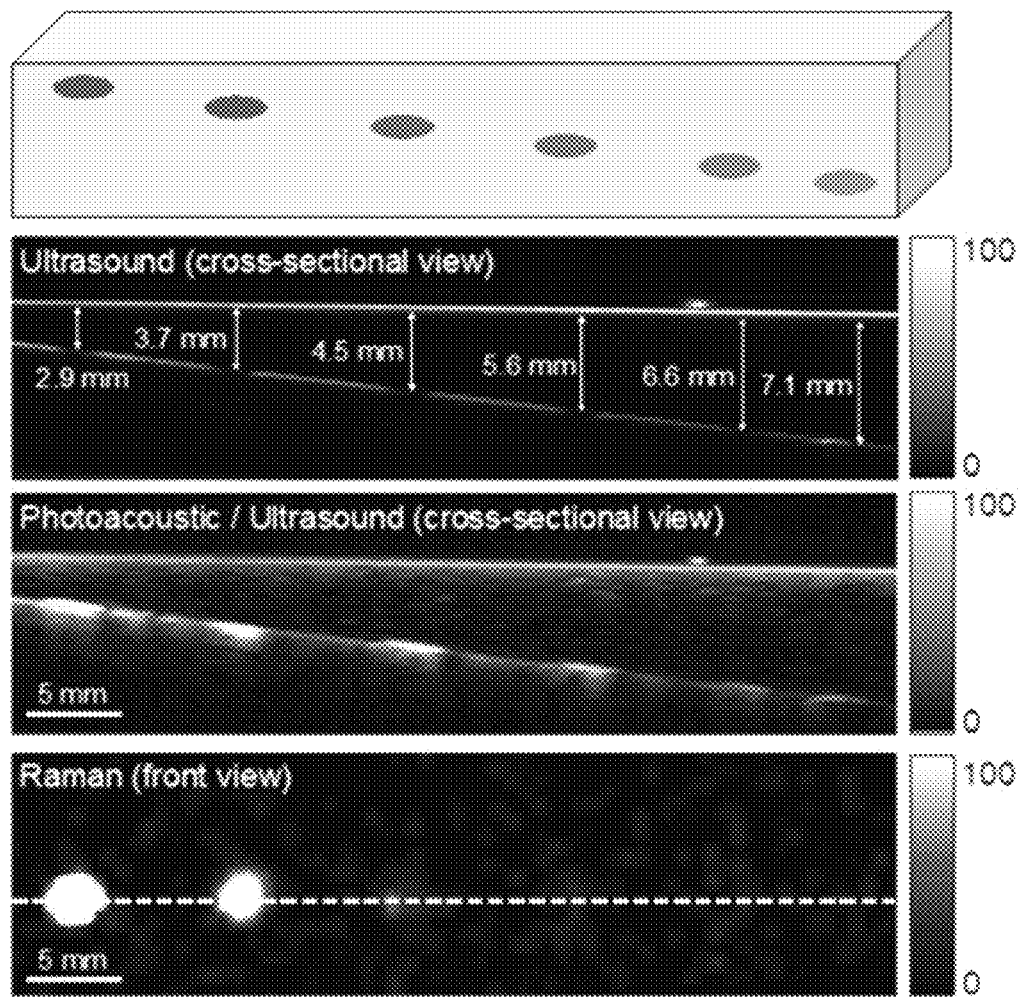
FIG. 1.12

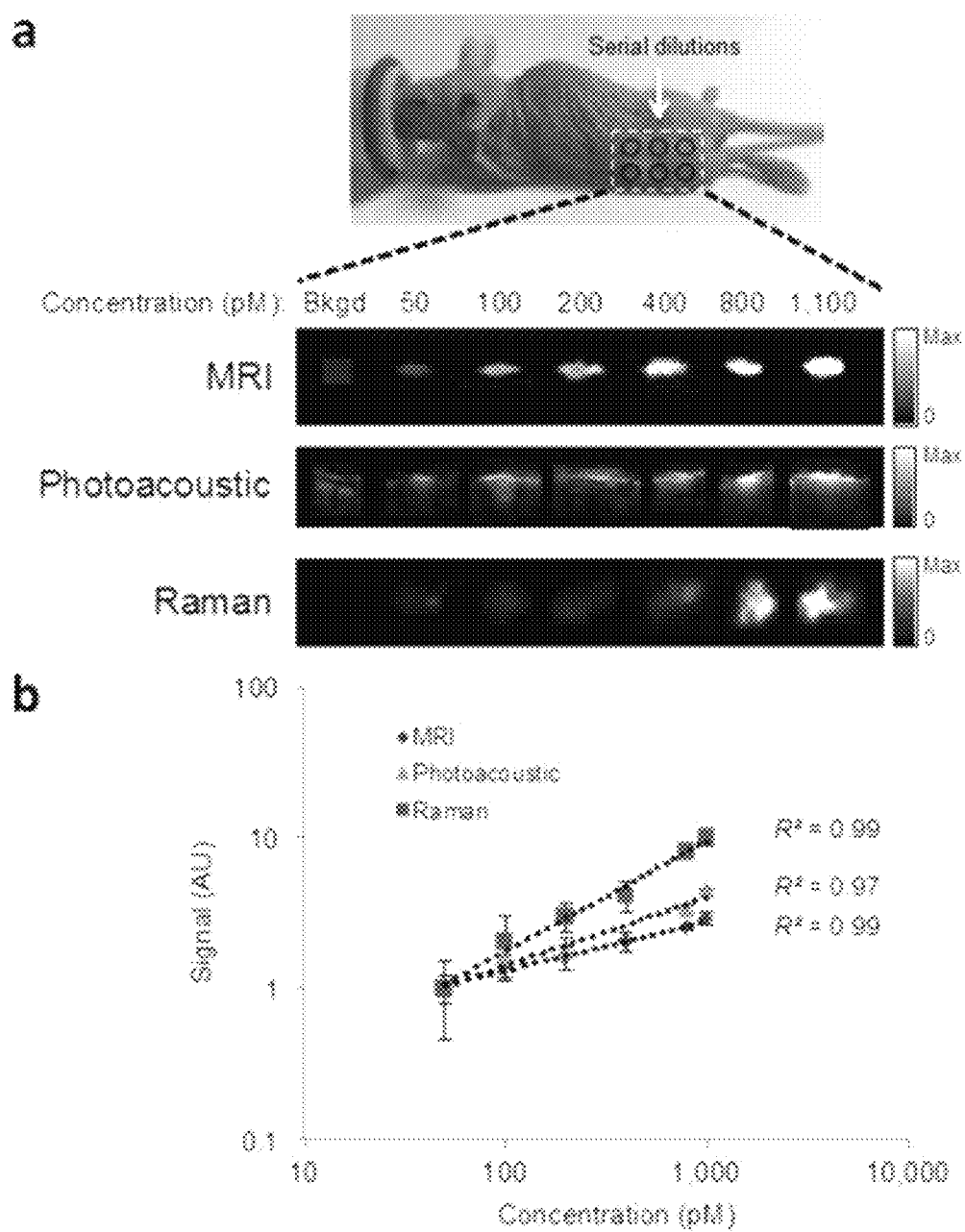
FIG. 1.13

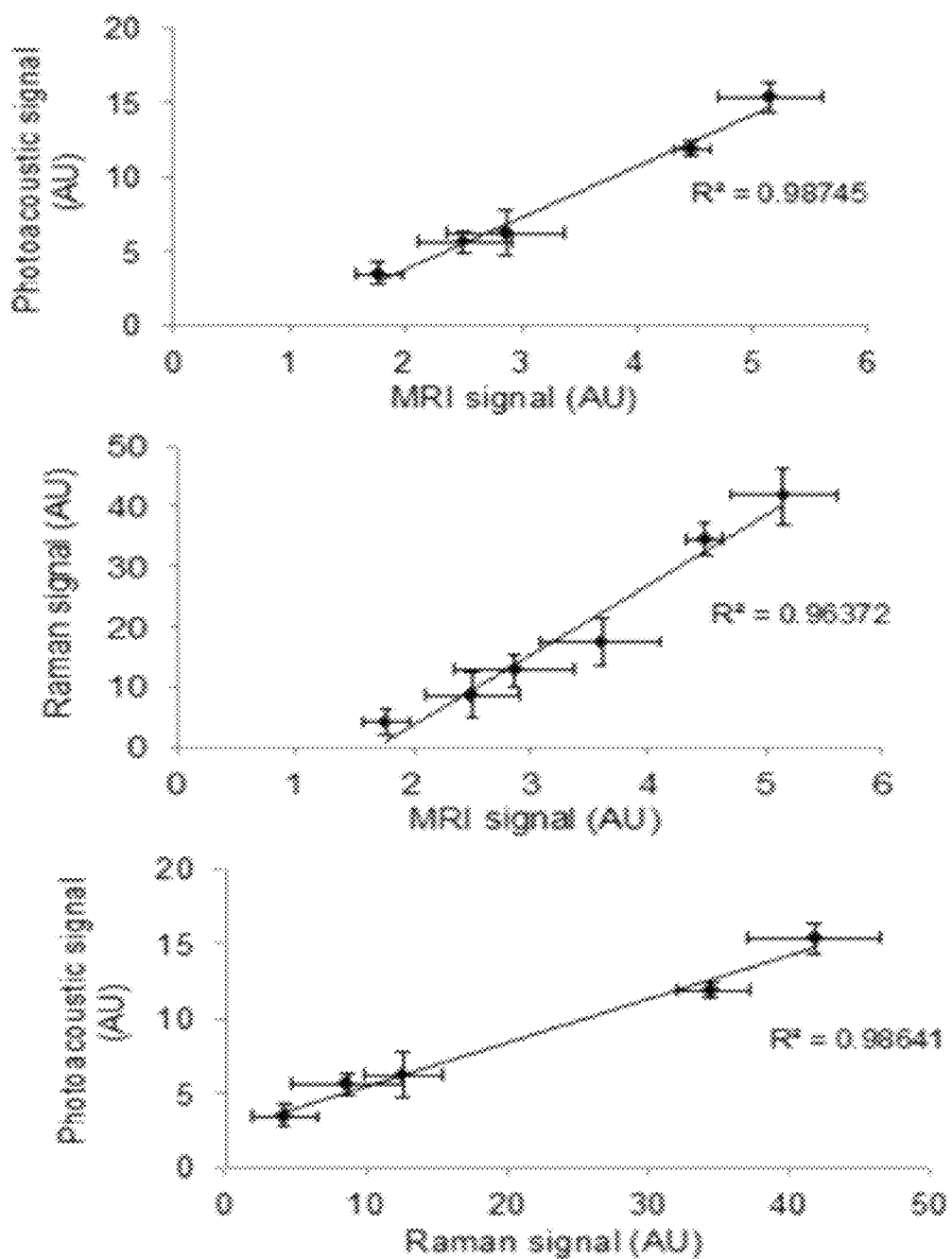
FIG. 1.14

FIG. 1.15

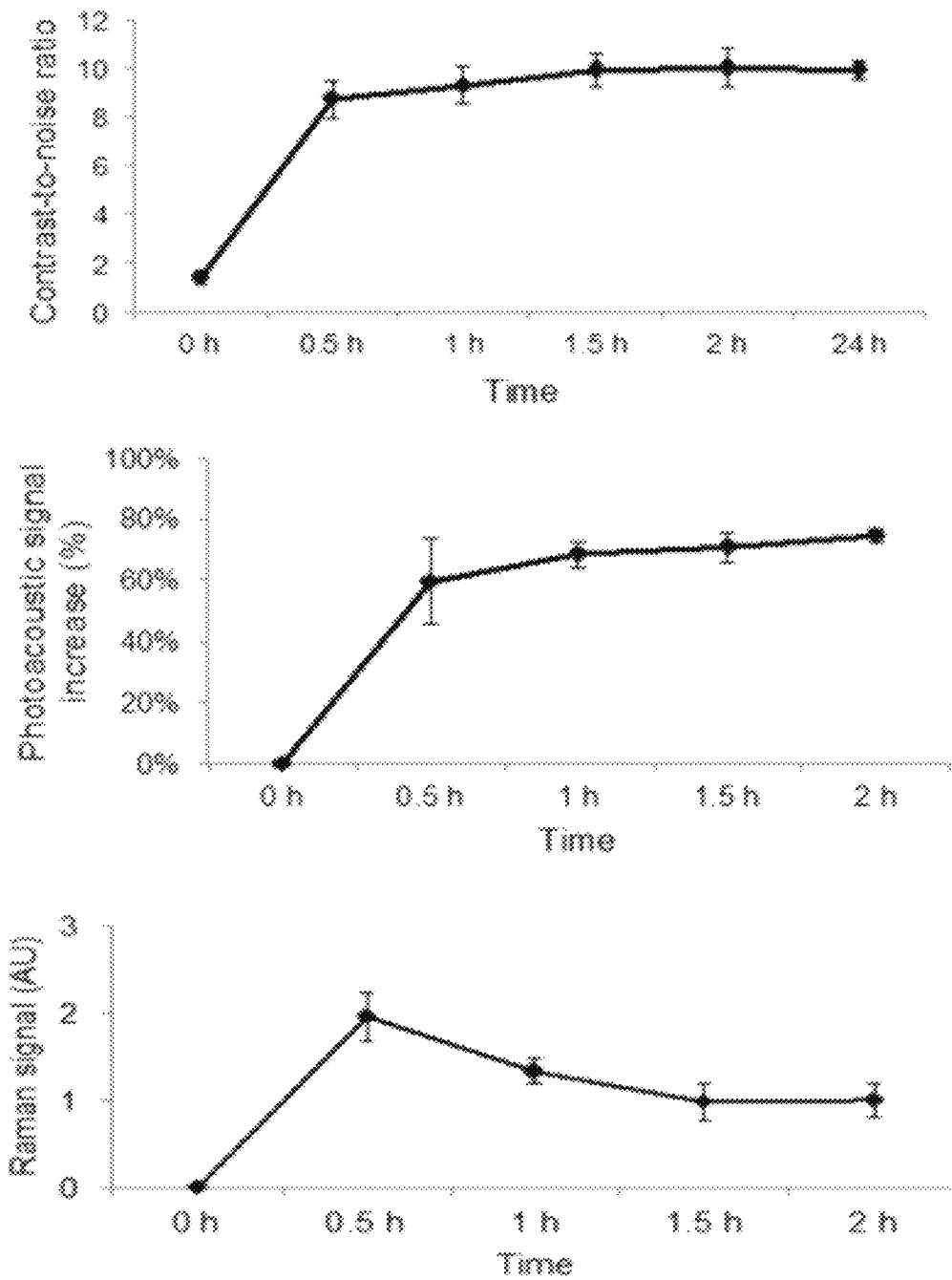
FIG. 1.16

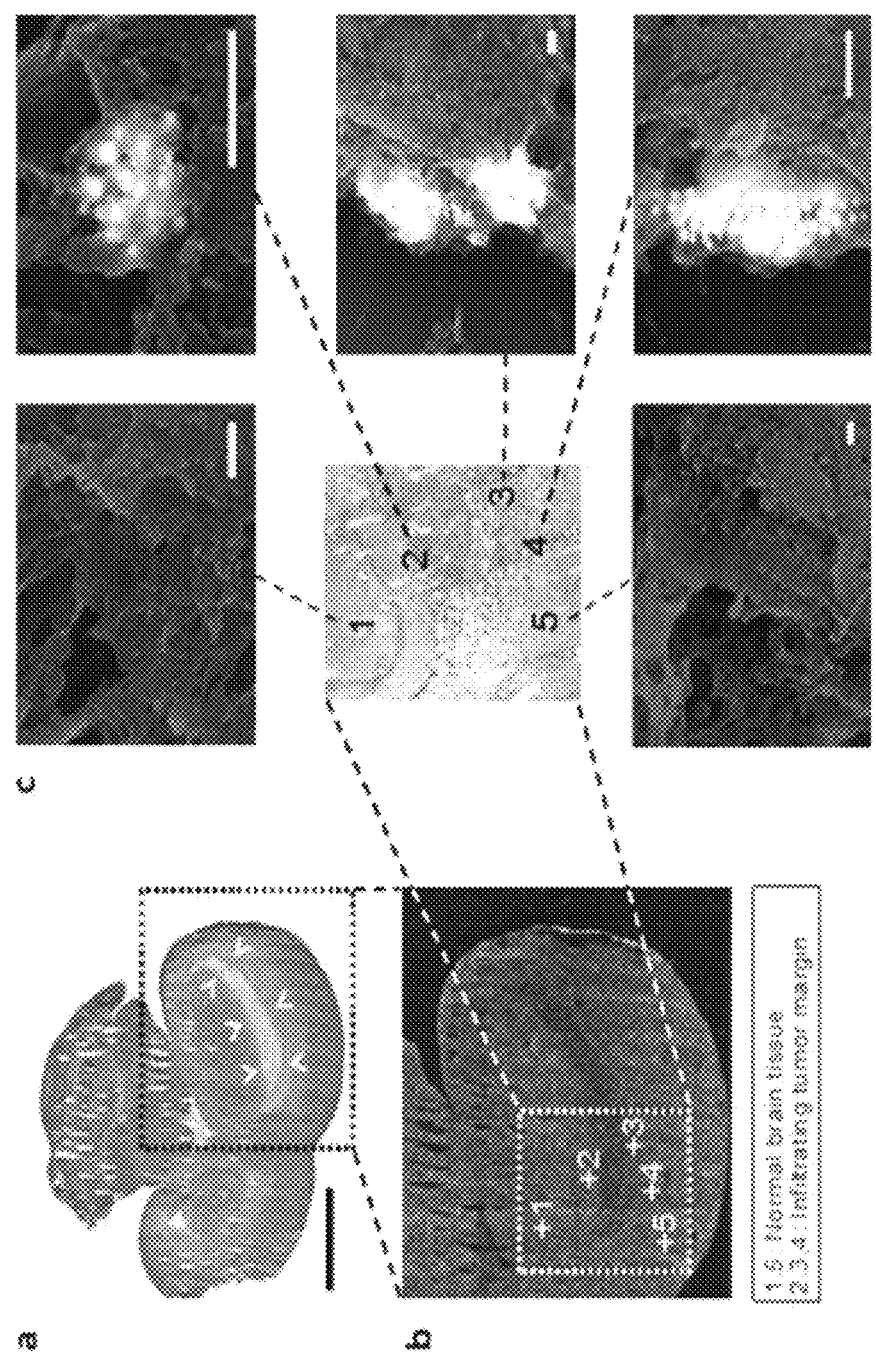
FIG. 1.17

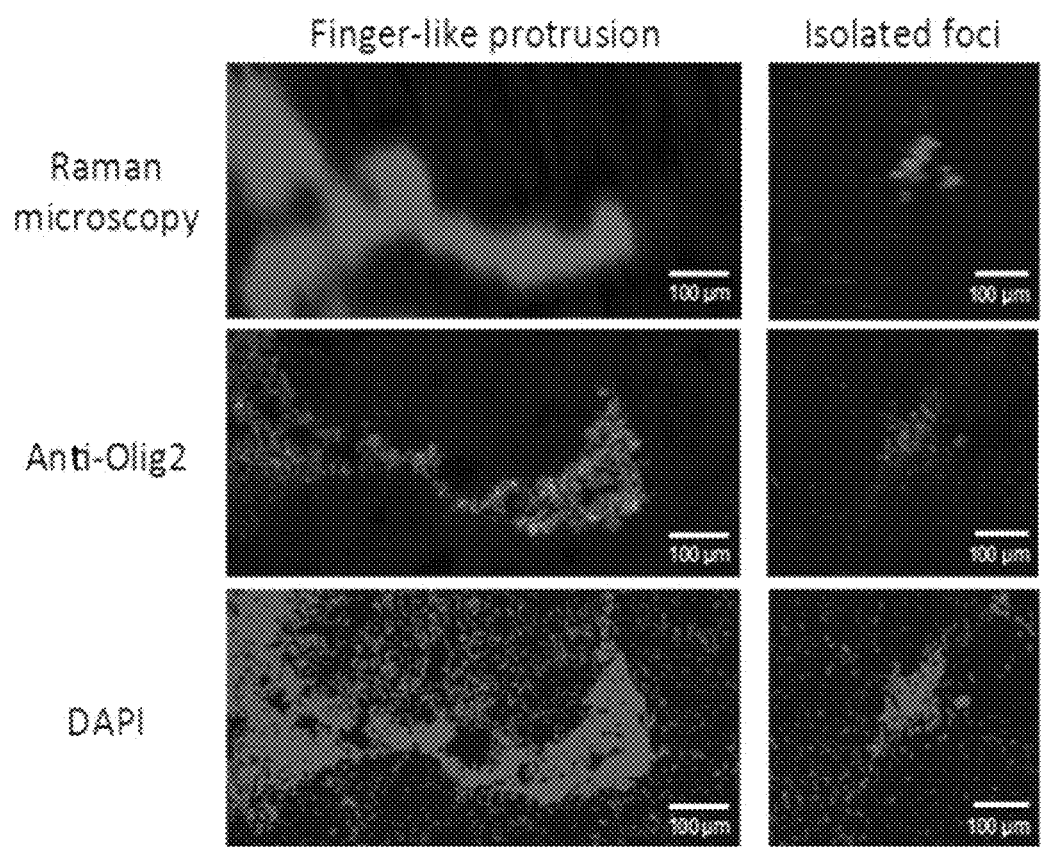
FIG. 1.18

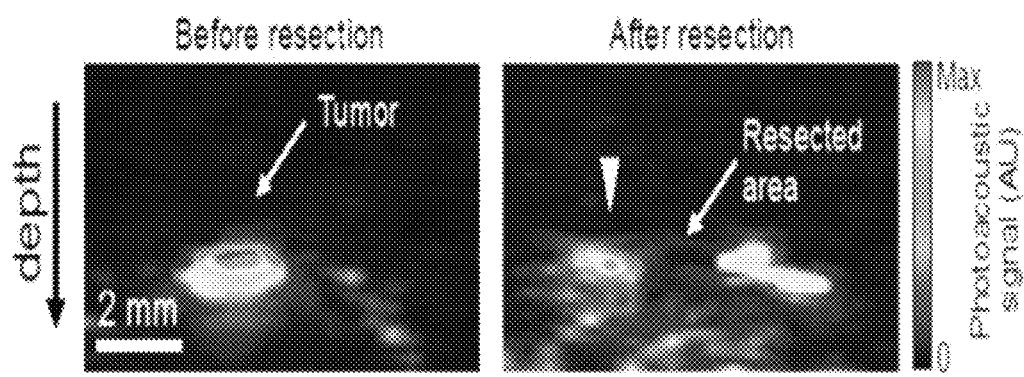
FIG. 1.19
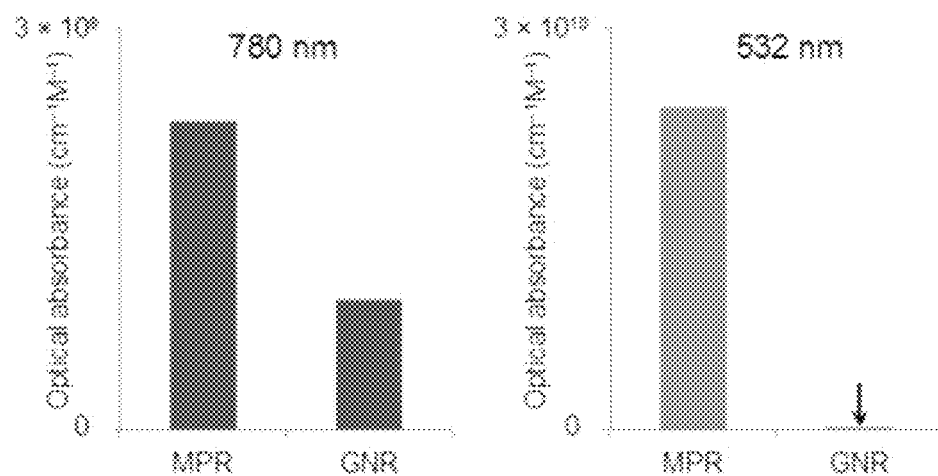
FIG. 1.20

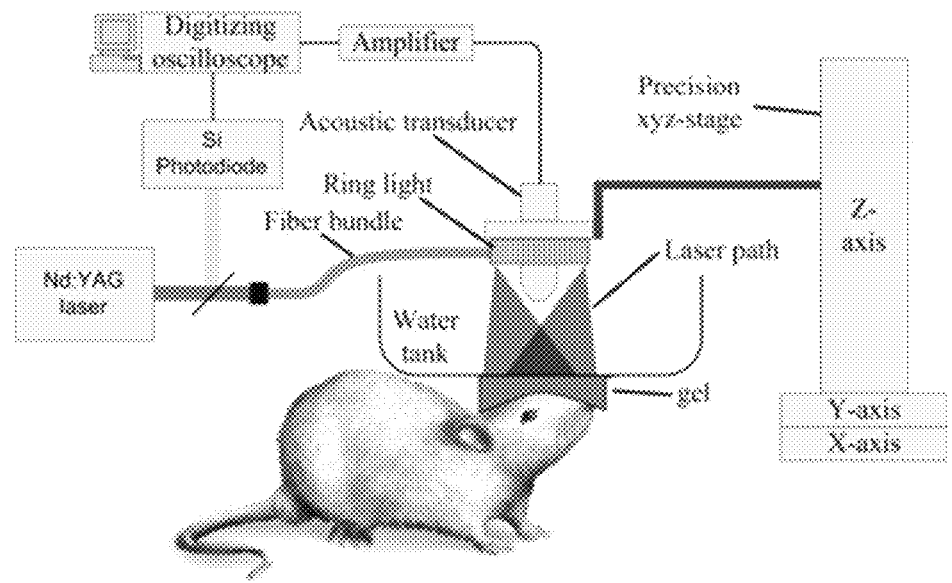
FIG. 1.21
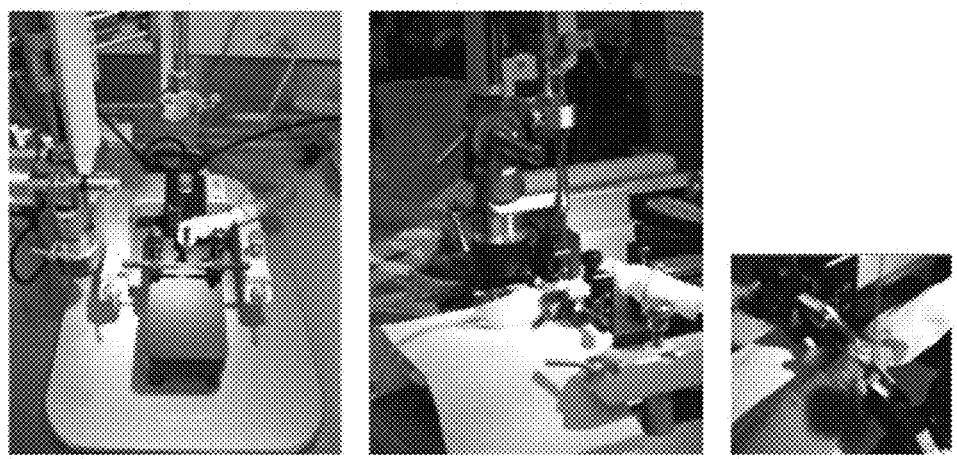
FIG. 1.22

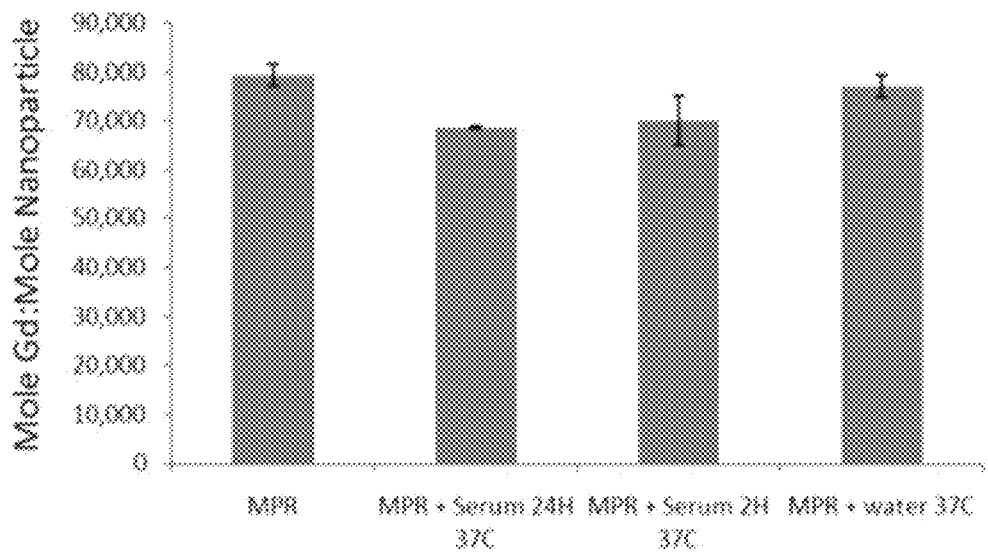
FIG. 2.1
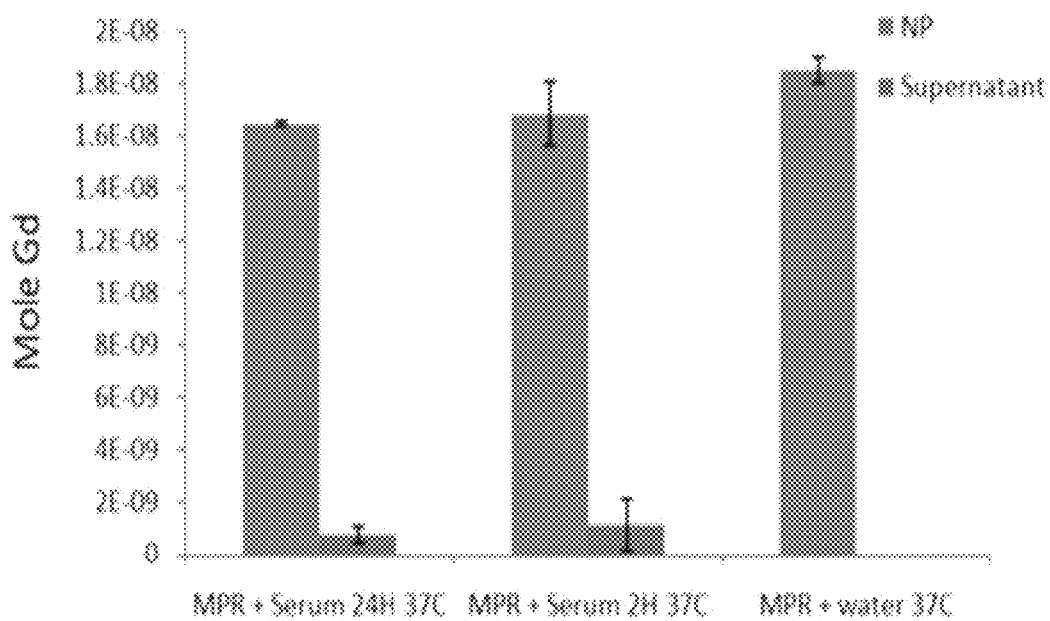
FIG. 2.2

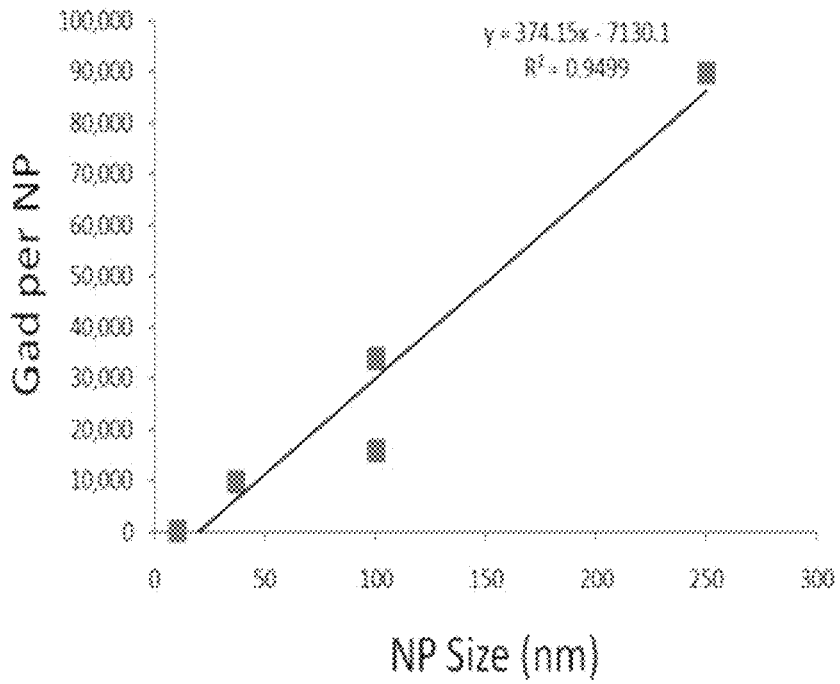
300 Gd:NP – Chen; J. Phys. Chem. C 2007, 111, 12542-12551
10,000 Gd:NP – Lin; Angew. Chem. Int. Ed. 2007, 46, 3680 –3682
16,000 Gd: NP – Mericle; Adv. Mater, 2005, 17, 2165
34,000 – Moudgil; Chem. Mater. 2008, 20, 6087–6094
90,000 – Wickline; Magnetic Resonance in Medicine 51:480–486 (2004)
FIG. 2.3

PROBES, METHODS OF MAKING PROBES, AND METHODS OF USE

CROSS-REFERENCE TO RELATED APPLICATION

This application claims priority to U.S. provisional application entitled "PROBES, METHODS OF MAKING PROBES, AND METHODS OF USE," having Ser. No. 61/430,776, filed on Jan. 7, 2011, which is entirely incorporated herein by reference.

FEDERAL SPONSORSHIP

This invention was made with Government support under contracts CA114747, CA118681, and CA119367 awarded by the National Institutes of Health. The Government has certain rights in the invention.

BACKGROUND

The completeness of the surgical resection is an important factor for the prognosis of brain tumor patients. In trying to achieve more complete glioma resections, the surgeon encounters several hurdles, which include irregular and indistinct tumor margins as well as tumor growth adjacent to or invading crucial neurological structures. A wide variety of techniques have been explored to date in an effort to better visualize tumor margins. For instance, pre-operative magnetic resonance imaging (MRI) has been used to guide stereotactic surgery, where the MR images are used to determine the macroscopic outline of the tumor. However, these methods suffer from limited spatial resolution and incongruencies between pre-operative MRI and actual tumor borders during surgery due to brain shift. Intra-operative MRI usually requires the administration of gadolinium (Gd)-chelates, which suffer from short blood half-life requiring repeated injections, high dosages and inaccuracies due to surgically induced false-positive contrast enhancement. Several intra-operative optical methods have been suggested, either based on intrinsic tissue optical properties or exogenous contrast agents. However, these optical techniques suffer from poor specificity due to tissue autofluorescence, limited resolution and depth of penetration, which ultimately limit localization of the true brain tumor margins.

SUMMARY

Embodiments of the present disclosure provide for probes, methods of using the probe, methods of making the probe, method of imaging a condition (e.g., pre-cancerous tissue, cancer, or a tumor), methods of planning resection of a brain tumor, methods of imaging a brain tumor, and the like.

An embodiment of the probe, among others, includes: a nanoparticle core, a reporter compound layer disposed on the core, an encapsulant material disposed around the reporter compound layer and the core, and a plurality of MRI agents disposed on the encapsulant material; wherein the core is a photoacoustic probe having a detectable photoacoustic signal; wherein the reporter compound is a Raman-active reporter, wherein the interaction of the Raman-active reporter with the core produces a detectable vibrational signal; wherein the MRI agents have a detectable MRI signal.

An embodiment of the method of planning a resection of a brain tumor, among others, includes: receiving a first information set corresponding to one or more of: a brain tumor localization and a macroscopic delineation; receiving a second information set corresponding to the brain tumor with deep tissue penetration; and receiving a third information set corresponding to the brain tumor margin; using the first information set, the second information set, and the third information set, to determine the location of one or more of: the brain tumor and the brain tumor margin, during an operative procedure selected from: a pre-operative procedure, an intra-operative procedure, and a combination thereof.

An embodiment of the method of imaging a brain tumor, among others, includes: obtaining a MRI signal, wherein the MRI signal is used to produce an image corresponding to one or more of: the localization of the whole brain tumor, macroscopic delineation of the whole brain tumor, and residual brain tumor; obtaining a photoacoustic signal, wherein the photoacoustic signal is used to produce an image corresponding to the brain tumor with deep tissue penetration; obtaining a Raman vibrational signal, wherein the Raman vibrational signal is used as a guide to defining the brain tumor margins; and producing an image of the brain tumor and the brain tumor margins using the MRI signal, photoacoustic signal, and Raman vibrational signal.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 1.1 illustrates a schematic of triple-modality Magnetic resonance imaging-Photoacoustic imaging-Raman imaging nanoparticle (MPR) concept. The Top portion shows that the MPRs are injected intravenously into a mouse bearing an orthotopic brain tumor. As the nanoparticles circulate in the blood stream, they diffuse through the disrupted blood-brain-barrier and are then sequestered and retained by the tumor. The MPRs are too large to cross the intact blood-brain-barrier and therefore cannot accumulate in healthy brain. The Bottom portion shows the concept of proposed eventual clinical use. Detectability by MRI allows pre-operative detection and surgical planning. Due to the retention of the probe, only one injection is necessary and the probe can be detected in the tumor during surgery several days later. Photoacoustic imaging with its relatively high resolution and deep tissue penetration is then able to guide bulk tumor resection intra-operatively. Raman imaging with its ultrahigh sensitivity and spatial resolution can then be used to remove residual microscopic tumor burden. Resected specimen can subsequently be examined with a Raman probe ex vivo to verify clear margins.

FIG. 1.2 illustrates the characterization of the MPRs. FIG. 1.2a is a simplified diagram of the MPR. A 60 nm gold core is surrounded by a thin Raman active layer that is protected by a 30 nm silica coating. The silica coating was further functionalized with maleimide-DOTA-Gd, which was conjugated to the thiol group on the silica. FIG. 1.2b illustrates electron microscopy (STEM) images of MPRs. FIG. 1.2c illustrates the particle relaxivity derived from T1 maps of probe dilutions in MRI phantoms. Data represent mean of two separate phantoms containing separate probe conjugations (error bars (s.e.m.) indicate batch-to-batch variation). Inset: T1 map of a MRI phantom containing MPRs at concentrations ranging from 3.2 nM (1) to 25 pM (8). FIG. 1.2d illustrates the optical absorbance of MPRs. FIG. 1.2e illustrates the Raman spectrum of MPRs with characteristic peaks at 1,021 $cm^{-1}$, 1,204 $cm^{-1}$, 1,340 $cm^{-1}$, 1,614 $cm^{-1}$, and 1,638 $cm^{-1}$. FIGS. 1.2f and 1.2g illustrate that during 30 min of continuous laser irradiation, the optical absorbance (FIG. 1.2f) and the Raman signal (FIG. 1.2g) remained constant.

FIG. 1.3 illustrates the triple-modality detection of brain tumors in living mice with MPRs. Three weeks after orthotopic inoculation, tumor-bearing mice (n=4) were injected intravenously with MPRs (16 nM, 170 µl). Photoacoustic, Raman and MR images of the brain (skin and skull intact) were acquired before and 2 h, 3 h and 4 h after injection, respectively. FIG. 1.3a illustrates the 2D axial MRI, Photoacoustic and Raman images. The post-injection images of all three modalities demonstrated clear tumor visualization. The Photoacoustic and Raman images were co-registered with the MR image, demonstrating good co-localization between the three modalities. FIG. 1.3b illustrates the 3D-rendering of MR images with the tumor segmented (red; top); overlay of 3D Photoacoustic images (green) over MRI (middle); and overlay of MRI, segmented tumor and Photoacoustic image (bottom) showing good co-localization of the Photoacoustic signal with the tumor. FIG. 1.3c illustrates the quantification of signal in the tumor shows significant increase in MRI, Photoacoustic and Raman signals before versus after the injection ("*" indicates P <0.001, "" indicates P<0.01). Error bars represent s.e.m.

FIG. 1.4 illustrates the histological validation. Upper row: 10 µm frozen sections from the margin of an eGFP+U87MG brain tumor were stained for eGFP (green) to visualize the tumor margins and CD11b (red) to visualize glial cells and were examined by laser scanning confocal microscopy. Bottom row: A 50 µm adjacent slice was examined by Raman microscopy to visualize the distribution of the MPRs. Note the Raman signal corresponding to the eGFP+ cells, indicating the presence of the probe in the tumor but not in the adjacent healthy tissue. The Raman signal (red) was scaled from 0 to 100 (AU). Boxes are not drawn to scale. STEM images verified the presence of MPRs in the brain tissue, while no MPRs were seen in the healthy brain tissue.

FIG. 1.5 illustrates a Raman-guided intra-operative surgery using MPRs. FIG. 1.5a illustrates a living tumor-bearing mice (n=3) underwent craniotomy under general anesthesia. Quarters of the tumor were then sequentially removed (as illustrated in the photographs) and FIG. 1.5b illustrates an intra-operative Raman imaging was performed after each resection step, until the entire tumor had been removed by visual inspection. After the gross removal of the tumor, several small foci of Raman signal were found in the resection bed (outlined by dashed white square; some Raman images smaller than black square). Raman color scale in red from −40 to 0 dB. FIG. 1.5c illustrates the subsequent histological analysis of sections from these foci demonstrated an infiltrative pattern of the tumor in this location, forming finger-like protrusions extending into the surrounding brain tissue. As shown in the Raman microscopy image (right), Raman signal was observed within these protrusions, indicating the selective presence of MPRs in these protrusions. The box is not drawn to scale. Raman signal in linear red color scale.

FIG. 1.6 illustrates the optical serum stability of MPRs. The MPRs showed a high level of optical stability when exposed to serum. Over the course of 22 h, the optical absorbance of a vial containing 50% serum only (blue curve) and a vial containing MPRs with 50% serum (red curve) were monitored. The blue and red curves show a slight increase of absorbance over time, an effect which is likely due to the evaporation of water from the vials, thereby increasing the concentration of serum in the vial. The green curve represents the subtraction of the "serum only" curve from the "MPR in serum" curve.

FIG. 1.7 illustrates the stability of the MPR hydrodynamic size during serum incubation. MPRs were incubated with 50% mouse serum/50% PBS for 24 h at 37° C. Hydrodynamic measurements of the samples taken with a dynamic light scattering instrument indicated that the particles' hydrodynamic size is stable over the course of 24 h of serum incubation.

FIG. 1.8 illustrates the stability of Raman spectrum before vs. after maleimide-DOTA-Gd conjugation. Raman spectra of MPRs before (blue curve) and after (dashed red curve) conjugation of maleimide-DOTA-Gd are virtually identical.

FIG. 1.9 illustrates the detection of MPRs in vitro. FIG. 1.9a illustrates an agarose phantom containing increasing concentrations of MPRs was scanned with MRI (upper row), Photoacoustic (middle row), and Raman (bottom row) instruments. The experiment was performed in triplicate. MRI was able to detect concentrations as low as 4.9 pM. The Photoacoustic and Raman imaging systems were able to detect even lower concentrations as low as 1.2 pM. FIG. 1.9b illustrates the MRI, Photoacoustic and Raman signals increased linearly with the MPR concentration ($R^2$=0.97, 0.99 and 0.99, respectively). Error bars represent s.e.m.

FIG. 1.10 illustrates the Raman ex vivo detection threshold. The phantom shown in FIG. 1.9 was extended to two additional lower concentrations (300 and 610 fM) to demonstrate the true Raman detection threshold. The lowest concentration detectable was 610 fM (note that a different image scale was used here than in FIG. 1.9 to allow visualization of these low concentrations. Black color still represents true zero Raman signal.

FIG. 1.11 illustrates the inter-modality signal correlation in phantom: MRI vs. Photoacoustic (top), MRI vs. Raman (middle), Raman vs. Photoacoustic (bottom).

FIG. 1.12 illustrates the superiority of Photoacoustic imaging in visualizing deep objects. A tissue mimicking phantom with 6 inclusions containing MPRs at increasing depths (upper diagram) was scanned with ultrasound (grayscale), Photoacoustic (green color scale) and Raman (red color scale) imaging systems. The ultrasound image reveals the depth of the inclusions while the Photoacoustic and Raman images depict the imaging signal emitted by the MPRs. While the Photoacoustic image clearly visualized all 6 inclusions, the Raman imaging instrument was capable of visualizing only the first 3 inclusions, up to a depth of 4.5 mm. The white dashed line on the Raman image represents the location of the Photoacoustic and ultrasound cross sectional image slices. The color scale bars show relative signal.

FIG. 1.13 illustrates the detection of MPRs in living mice. FIG. 1.13a illustrates the MPRs ranging in concentrations from 50 pM to 1100 pM were injected subcutaneously into the flank of living mice (n=3) and scanned with MRI, Photoacoustic and Raman instruments. MRI and Photoacoustic imaging clearly visualized the 100 pM concentration, while the 50 pM concentration showed signal close to the background (bkgd; muscle) level. The Raman image, however, clearly showed a distinct signal from the 50 pM well. FIG. 1.13*b* illustrates the MRI, Photoacoustic and Raman signals recorded in vivo increased linearly with the MPR concentration ($R^2$=0.99, 0.97 and 0.99 respectively). Error bars represent s.e.m.

FIG. 1.14 illustrates the inter-modality signal correlation in vivo: MRI vs. Photoacoustic (top), MRI vs. Raman (middle), Raman vs. Photoacoustic (bottom).

FIG. 1.15 illustrates the coronal reformation of the Photoacoustic-MRI overlay (taken from FIG. 1.3), illustrating the three-dimensional nature of Photoacoustic imaging.

FIG. 1.16 illustrates the MPR in vivo signal kinetics. Unlike the MRI (top) and Photoacoustic (middle) kinetic curves, the Raman (bottom) kinetic curve showed an initial peak at 0.5 h, followed by a decrease to a plateau at 1.5 h. This effect is presumably due to initial nonspecific circulation of MPRs in superficial layers, before clearance of MPRs from the blood-stream has occurred. Raman is most sensitive to superficial layers such as the skin because of the proximity of the lens to the skin surface of the animal. Error bars represent s.e.m.

FIG. 1.17 illustrates the MPRs accumulate in infiltrating tumor margins in an orthotopic primary human glioblastoma (GBM) xenograft mouse model. Tumor-bearing mice were injected intravenously with MPRs (150 µl, 16 nM, n=4). At 24 h post-injection, brains were excised and cryosections (10 µm slice thickness) were stained with hematoxylin and eosin (H&E) and subsequently analyzed with a scanning electron microscope (SEM). Adjacent sections were stained with Olig2-specific immunohistochemistry (center image). FIG. 1.17*a* illustrates the H&E stain of the brain showing a tumor in the right hemisphere (boxed region). FIG. 1.17 illustrates an SEM scan of this H&E section was then acquired to sample high magnification SEM images from precise locations of the tumor and surrounding brain parenchyma (exact sample locations indicated by '+' signs). FIG. 1.17*c* illustrates the higher magnification SEM images taken from five different locations in the brain were acquired (overlay of secondary electron SEM on backscattered electron SEM, MPRs shown as white dots). Location 1 and 5 represent normal brain tissue as confirmed by IHC, whereas locations 2-4 represent zones of infiltrating tumor margin. Note that many clusters of MPRs were found not only in the bulk tumor but indeed also in the diffusely infiltrating margins of the tumor. Scale bar in FIG. 1.17*a* equals 2.5 mm; scale bar in all SEM images equals 500 nm.

FIG. 1.18 illustrates MPRs that visualize finger-like protrusions and isolated foci in an orthotopic primary human glioblastoma (GBM) xenograft mouse model. Tumor-bearing mice were injected intravenously with MPRs (150 µl, 16 nM, n=4). At 24 h post-injection, brains were excised and cryosections were analyzed with Raman microscopy (500 µm slice thickness) and Olig2-specific immunofluorescent staining of an adjacent section (with DAPI counterstain; 10 µm slice thickness). The Raman signal (red) represents the location of the MPRs, the Olig-2 signal (green) the presence of tumor cells and DAPI (blue) the presence of cellular nuclei of both tumor and surrounding brain (Note that certain differences in co-localization between Raman signal and Olig2/DAPI staining are expected as these images are not taken from the exact same section and volume averaging in the Raman image due to the larger slice thickness can occur). Left column: A finger-like tumor protrusion is shown at the edge of the brain tumor. As demonstrated by the good co-localization of the Raman and Olig-2 signal, MPRs accumulated in and were therefore able to outline such a finger-like protrusion. Right column: An isolated satellite metastasis away from the main tumor is also depicted by Raman imaging (note the good co-localization of red and green signal). Data is representative of three random slices through each of the four tumors.

FIG. 1.19 illustrates intra-operative Photoacoustic imaging. A mouse bearing a glioblastoma tumor (primary human xenograft) was injected with MPRs (150 µl, 16 nM). After 24 h, the brain was perfused with PBS, excised, and embedded in an agarose gel. Coronal Photoacoustic images were acquired before (left image) and after (right image) partial tumor resection. An absence of Photoacoustic signal in the resected portion of the tumor was observed, while residual Photoacoustic signal (arrow-head) was observed in the area of the non-resected tumor. Note that the increased grayscale ultrasound signal to the right of the resected cavity is likely due the surgical manipulation, an effect that is commonly observed during surgery. Photoacoustic images (color scale from 0 to max) were overlaid on conventional ultrasound images (gray), which outline the gross anatomy of the mouse brain.

FIG. 1.20 illustrates a comparison of MPRs to gold nanorods-780 (GNRs) at near-infrared and visible wavelengths. While the absorbance of MPRs is ~2.5-fold higher than GNRs (10 nm diameter, 38 nm length) at 780 nm (red bars), it is 123-fold higher than GNRs at 532 nm (green bars). The data are taken from the optical absorbance spectra shown in FIG. 1.2*d*.

FIG. 1.21 illustrates a photoacoustic imaging instrument. A tunable pulsed laser (Nd:YAG laser) illuminated the subject through a fiber optic ring light. The Photoacoustic signals produced by the sample were acquired using either a 5 MHz or 25 MHz focused transducer. A precision xyz-stage was used to move the transducer and the fiber ring along a planar 2D trajectory. The time of arrival and the intensity of the laser pulses were recorded using a silicon photodiode. This information was used to synchronize the acquisition and compensate for pulse-to-pulse variations in laser intensity. The analog Photoacoustic signal was amplified using a 30 dB preamplifier and digitized using an oscilloscope.

FIG. 1.22 illustrates a stereotactic brain tumor implantation.

FIG. 2.1 illustrates a graph of the mole ratios of Gd to MPR.

FIG. 2.2 illustrates a graph of the amount of gadolinium dissociated from MPR and in solvent.

FIG. 2.3 illustrates a graph of the loading versus the size of the nanoparticle.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of imaging, chemistry, synthetic organic chemistry, biochemistry, biology, molecular biology, microbiology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in °C., and pressure is at or near atmospheric. Standard temperature and pressure are defined as 20°C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

The term "detectable" refers to the ability to detect a signal over the background signal.

The term "acoustic detectable signal" is a signal derived from a nanoparticle core that absorbs light and converts absorbed energy into thermal energy that causes generation of acoustic signal through a process of thermal expansion. The acoustic detectable signal is detectable and distinguishable from other background acoustic signals that are generated from the subject or sample. In other words, there is a measurable and statistically significant difference (e.g., a statistically significant difference is enough of a difference to distinguish among the acoustic detectable signal and the background, such as about 0.1%, 1%, 3%, 5%, 10%, 15%, 20%, 25%, 30%, or 40% or more difference between the acoustic detectable signal and the background) between acoustic detectable signal and the background. Standards and/or calibration curves can be used to determine the relative intensity of the acoustic detectable signal and/or the background.

The term "acoustic signal" refers to a sound wave produced by one of several processes, methods, interactions, or the like (including light absorption) that provides a signal that can then be detected and quantitated with regards to its frequency and/or amplitude. The acoustic signal can be generated from one or more nanoparticle cores of the probes of the present disclosure. In an embodiment, the acoustic signal may need to be sum of each of the individual photoacoustic signals. In an embodiment, the acoustic signal can be generated from a summation, an integration, or other mathematical process, formula, or algorithm, where the acoustic signal is from one or more probes. In an embodiment, the summation, the integration, or other mathematical process, formula, or algorithm can be used to generate the acoustic signal so that the acoustic signal can be distinguished from background noise and the like. It should be noted that signals other than the acoustic signal can be processed or obtained is a similar manner as that of the acoustic signal.

The acoustic signal or acoustic energy can be detected and quantified in real time using an appropriate detection system. One possible system is described in the following references: Journal of Biomedical Optics-March/April 2006-Volume 11, Issue 2, 024015, Optics Letters, Vol. 30, Issue 5, pp. 507-509, each of which are included herein by reference. In an embodiment, the acoustic energy detection system can includes a 5 MHz focused transducer (25.5 mm focal length, 4 MHz bandwidth, F number of 2.0, depth of focus of 6.5 mm, lateral resolution of 600 μm, and axial resolution of 380 μm. A309S-SU-F-24.5-MM-PTF, Panametrics), which can be used to acquire both pulse-echo and photoacoustic images. In addition, high resolution ultrasound images can also be simultaneously acquired using a 25 MHz focused transducer (27 mm focal length, 12 MHz bandwidth, F number of 4.2, depth of focus of 7.5 mm, lateral resolution of 250 μm, and axial resolution of 124 μm. V324-SU-25.5-MM, Panametrics). Other detection strategies including capacitive micromachined ultrasonic transducers (CMUT) arrays can also be used to detect the acoustic signal.

The term "Surface-Enhanced Raman Scattering (SERS)" refers to the increase in Raman scattering exhibited by certain molecules in proximity to certain metal surfaces. (see, U.S. Pat. No. 5,567,628) The SERS effect can be enhanced through combination with the resonance Raman effect. The surface-enhanced Raman scattering effect is even more intense if the frequency of the excitation light is in resonance with a major absorption band of the molecule being illuminated. In short, a significant increase in the intensity of Raman light scattering can be observed when molecules are brought into close proximity to (but not necessarily in contact with) certain metal surfaces. The metal surfaces need to be "roughened" or coated with minute metal particles. The increase in intensity can be on the order of several million-fold or more. SERS can be present through the combination of the core and reporter compound layer used in probes of the present disclosure.

The term "reporter compound" can refer to a Raman-active label. The term "Raman-active label" can refer to a substance that produces a detectable Raman spectrum, which is distinguishable from the Raman spectra of other components present, when illuminated with a radiation of the proper wavelength.

The term "nanoparticle" refers to matter synthetically tuned to a size regime of about 1 and 1000 nm, about 1 to 500 nm, or about 1 to 250 nm.

The term "silica" refers to polymeric $SiO_2$ which can contain other dopants and/or alloys and may vary widely in porosity and hardness.

The term "dispose" describes the permanent or temporary attachment of matter to a supporting material.

The term "illuminating" as used herein refers to the application of a light source, including near-infrared (NIR), visible light, including laser light capable of exciting dyes and nanoparticle cores of the embodiments of the probes herein disclosed.

The term "magnetic resonance imaging (MRI)" as used herein refers to a medical imaging technique most commonly used in radiology to visualize the structure and function of the body. It provides detailed images of the body in any plane. MRI uses no ionizing radiation, but uses a powerful magnetic field to align the nuclear magnetization of (usually) hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body. When a subject lies in a scanner, the hydrogen nuclei (i.e., protons) found in abundance in an animal body in water molecules, align with the strong main magnetic field. A second electromagnetic field that oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different tissues of the body (e.g., fat versus muscle) realign at different speeds, the different structures of the body can be revealed. Contrast agents may be injected intravenously to enhance the appearance of blood vessels, tumors or inflammation. MRI is used to image every part of the body, but is particularly useful in neurological conditions, disorders of the muscles and joints, for evaluating tumors and showing abnormalities in the heart and blood vessels.

The term "positive contrast" as used herein refers to the differences in the observed MRI image between that of a targeted tissue site that generates a greater detectable signal intensity than the intensity of a signal generated in a surrounding tissue.

The term "negative contrast" as used herein refers to the difference in the observed MRI image between that of a targeted tissue site that has a lower detectable signal intensity than the intensity of a signal generated in a surrounding tissue.

The term "in vivo imaging" as used herein refers to methods or processes in which the structural, functional, or physiological state of a living being is examinable without the need for a life ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The term "sample" can refer to a tissue sample, cell sample, a fluid sample, and the like. The sample may be taken from a subject. The tissue sample can include brain, hair (including roots), buccal swabs, blood, saliva, semen, muscle, or from any internal organs, or cancer, precancerous, or tumor cells associated with any one of these. The fluid may be, but is not limited to, urine, blood, ascites, pleural fluid, spinal fluid, and the like. The body tissue can include, but is not limited to, brain, skin, muscle, endometrial, uterine, and cervical tissue or cancer, precancerous, or tumor cells associated with any one of these. In an embodiment, the body tissue is brain tissue or a brain tumor or cancer.

The term "administration" refers to introducing a probe of the present disclosure into a subject. One preferred route of administration of the compound is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the term "host," "subject," or "patient," includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

General Discussion

Embodiments of the present disclosure provides for probes, methods of using the probe, methods of making the probe, methods of imaging a condition (e.g., pre-cancerous tissue, cancer, or a tumor), methods of planning resection of a brain tumor, methods of imaging a brain tumor, and the like. Embodiments of the present disclosure can be used to image, detect, study, monitor, and/or evaluate, a condition or disease such as pre-cancerous tissue, cancer, or a tumor, specifically, brain cancer or a brain tumor.

In an embodiment of the present disclosure a probe can be administered in a single injection, for example, to a subject, which allows for pre-operative, intra-operative, and post-operative visualization of a tissue (e.g., pre-cancerous tissue, cancer, tumor, specifically a brain tumor) using the same probe in the same cells. In an embodiment, an operative procedure can include pre-operative, intra-operative, and post-operative, procedures and can span over a time from a of few hours, few days, to about a week to two weeks, depending upon the particular circumstances. The probe is sequestered and maintained by the brain tumor for a long period of time (e.g., about a week to two weeks) so that pre-operative, intra-operative, and post-operative visualization can be performed. Using the probe during the pre-operative and intra-operative procedure allows for deep visualization (e.g., about 1-5 cm) of the tumor and high sensitivity and specific detection of tumor margins. More specifically, the probe can be used to produce an MRI signal, a photoacoustic signal, and a Raman signal, which allow for brain tumor localization and macroscopic delineation, imaging of the brain tumor with deep tissue penetration (e.g., about 1-5 cm), and/or high sensitivity, high resolution, and high specificity, of the tumor margins and infiltrating tumor margins, respectively, during one or more portions of the procedure. Embodiments of the probe allow for visualization (e.g., imaging and/or detecting) of the same tumor tissue along the entire spectrum of diagnosis and surgical therapy, exploiting and combining the complementary strengths of each signal. In particular, the MRI signal permits non-invasive and depth-independent screening, detection, and staging and the photoacoustic and/or Raman signals can facilitate accurate tumor resection intro-operatively. It should be noted that each signal can be detected at each stage of the procedure, but one or a combination may be favored since some signals are more advantageous than others during different parts of the procedure. In an embodiment, each of the signals can be received (e.g., detected, obtained, generated, and the like). In an embodiment, one, two or three of the signals can be used to produce an image of the cancerous tissue. This process can be repeated at two or more stages of the operative procedure do facilitate resection planning and/or strategies to proceeding forward. Additional details are described in the Examples.

Embodiments of the probe can include a nanoparticle core, a reporter compound layer disposed on the core, an encapsulant material disposed around the reporter compound layer and the core, and a plurality of MRI agents disposed on the encapsulant material. The core is a photoacoustic probe with a detectable photoacoustic signal. In an embodiment, a photoacoustic signal can be generated by directing optical energy (e.g., a laser) toward the probe and the core absorbing the optical energy and converting the energy into thermal energy to produce an acoustic signal. The reporter compound is a Raman-active reporter, where the interaction of the Raman-active reporter with the core produces a detectable vibrational signal. The MRI agent has a detectable MRI signal. Each signal can be detected using a separate detection system or one or two systems can be combined to detect multiple agent types. Additional details regarding detection of the signals are provided in the Examples.

In general, the largest dimension of the probe can be about 10000 nm or less, about 5000 nm or less, about 2000 nm or less, about 1000 nm or less, about 500 nm or less, about 400 nm or less, about 300 nm or less, about 200 nm or less, about 100 nm or less, or about 50 nm or less. The phrase "or less" is greater than about 0 nm, or can be replaced with " . . . to about 1 nm", " . . . to about 5 nm", to about 10 nm, or " . . . to about 20 nm" (e.g., about 2000 nm or less→about 2000 nm to about 1 nm).

An embodiment of the core can have a spherical shape (e.g., about 75 to 100% spherical). Another embodiment of the core can be in the shape of a rod (e.g., hollow (can also referred to as a tube) or solid). It is contemplated that the core can have other shapes that are not spherical or rod shaped, but these two embodiments are discussed herein for clarity and other shapes are intended to be included herein. An additional embodiment can include a nanoparticle assembly with small nanoparticles condensing into a larger structure (e.g., about 2 to 10000 nanoparticles). An embodiment of the core can be made of a material such as: gold, silver, copper, iron-oxide, manganese, and a combination thereof.

In general, the largest dimension of the core can be less than about 1000 nm, can be about 500 nm or less, about 400 nm or less, about 300 nm or less, about 200 nm or less, or about 100 nm or less, with the smallest dimension being of a nanoparticle able to include a reporter compound layer, encapsulant, and MRI agents. In a particular embodiment, the dimensions of a spherical core can be about 10 to 150 nm, about 40 to 80 nm, or about 60 nm. In another embodiment, the dimensions of the rod shaped core can be about 5 to 15 nm in diameter and 35 to 55 nm in length, about 8 to 12 nm in diameter and 40 to 50 nm in length, or about 10 nm in diameter and 45 nm in length. In an embodiment, the dimensions of the rod are tuned to enhance or decrease SERS.

An embodiment of the probe can include a reporter compound layer disposed on a portion (e.g., 10% or more, 30% or more, 50% or more, or 70% or more) of or over the entire surface of the core as well as include multiple layers of reporter compounds. In other words, the reporter compounds can form a sub-monolayer, monolayer, or multilayer, on the surface of the core, wherein the reporter compound layer is capable of generating a SERS signal. In general, the reporter compound layer can have a thickness of about 0.1 to 5 nm. In an embodiment, the reporter compound layer can have a thickness of about 0.1 to 5 nm when the core is a sphere. In an embodiment, the reporter compound layer can have a thickness of about 0.1 to 5 nm when the core is a rod. In an embodiment, the thickness of the reporter compound layer can be designed based on the molecular weight and structure of the reporter compound.

Embodiments of the reporter compound can include Raman-active compounds that produce a SERS signal (e.g., unique SERS signature relative to probes made of different core materials or reporter compounds) in response to excitation by a laser or other light source. In an embodiment, the Raman-active organic compounds are polycyclic aromatic or heteroaromatic compounds. In an embodiment, the reporter compound can include, but is not limited to, 4-mercaptopyridine (4-MP); trans-4,4' bis(pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl) acetylenes; 3-ethyl-2-[7-(3-ethyl-2-benzothiazolinylidene)-1,3,5-heptatrienyl]benzothiazolium iodide (DTTC); Bodipy; TRIT (tetramethyl rhodamine isothiol); NBD (7-nitrobenz-2-oxa-1,3-diazole); Texas Red dye; phthalic acid; terephthalic acid; isophthalic acid; cresyl fast violet; cresyl blue violet; brilliant cresyl blue; para-aminobenzoic acid; methylene blue; toluidine blue; small peptides; erythrosine; biotin; digoxigenin; 5-carboxy-4',5'-dichloro-2',7'-dimethoxy fluorescein; 5-carboxy-2',4',5',7'-tetrachlorofluorescein; 5-carboxyfluorescein; 5-carboxy rhodamine; 6-carboxyrhodamine; 6-carboxyletramethyl amino phthalocyanines; azomethines; cyanines; xanthines; succinylfluoresceins; aminoacridine; fullerenes; organocyanides (e.g., isocyanide), and other similar asymmetric and/or aromatic compounds, and combinations thereof.

As mentioned above, the encapsulant encloses the reporter compound layer and the core. In addition, the MRI agent and other agents (e.g., drugs, targeting agents, etc) can attach directly or indirectly to the encapsulant. An embodiment of the encapsulant can include silica, metallic films (e.g., gold, silver, and the like) different from the core material, polymers including PEG and PLGA/PEG, and polymeric chelators (e.g., poly DOTA, dendrimer backbone, poly DTPA, or dendrimer alone). The thickness of the encapsulant for a spherical core can be about 0.1 to 200 nm or about 10 to 50 nm thick. The thickness of the encapsulant for a rod shaped core can be about 0.1 to 200 nm or about 3 to 30 nm thick.

In an embodiment, the amount or number of MRI agents disposed (e.g., directly or indirectly) on the encapsulant can be about 1 to 10,000,000 MRI agents or about 5000 to 500,000 MRI agents. In general, larger volumes of encapsulant contain larger numbers of MRI agents. In an embodiment all or a portion of the MRI agents can be directly disposed on the encapsulant surface. In other words, where the MRI agent is Gd, Gd is directly attached to the surface of the encapsulant and not attached via a linker compound such as DOTA via a maleimide linkage. In an embodiment, all or a portion of the MRI agents are indirectly disposed on the encapsulant surface via one or more linkers, such as DOTA when the MRI agent is Gd. In an embodiment, in addition to all of the MRI agents being directly disposed on the encapsulant or all being indirectly disposed on the encapsulant, the ratio of the MRI agent directly disposed on the encapsulant surface and MRI agent indirectly linked to the encapsulant surface is about 1:10 to about 10:1 or about 1:1. In an embodiment, the number of MRI agents directly attached and indirectly attached can be varied to achieve a certain signal.

In an embodiment, relatively more MRI agent (e.g., Gd) can be directly disposed on the encapsulant than can be indirectly disposed (e.g., DOTA-Gd) on the encapsulant, so in some instances a much stronger MRI signal can be generated by disposing the MRI agent directly on the encapsulant. See the Examples for additional details. The amount indirectly disposed can be controlled by pH, temperature, ionic strength, and/or identity of MRI agent/encapsulant. Thus, the amount attached directly and indirectly can be controlled and selected to achieve desired results.

An embodiment of the MRI agent can be Gd, iron oxide, paramagnetic chemical exchange saturation transfer (CEST) agents, $^{19}F$ active materials, manganese, melanin, or a substance that shortens or elongates T1 or T2 and a combination thereof. The Gd MRI agent can be a compound such as DOTA-Gd, DTPA-Gd, Gd within a polymeric chelator, and Gd immobilized by negative charges on the encapsulant. The iron oxide MRI agent can be a compound such as a small paramagnetic iron oxide (SPIO) or an ultrasmall SPIO with or without a dextran or other stabilizing layer. The paramagnetic CEST MRI agent can be a compound such as lanthamide complexes. The paramagnetic component of the MRI agents listed above can be directly or indirectly disposed on the encapsulant.

In an embodiment, the MRI agent can be linked to the encapsulant surface via a linkage such as a maleimide linkage, NHS ester, click chemistry, or another covalent or non-covalent approach or a combination thereof. In an embodiment, the MRI agents can also be loaded without addition of any exogenous agent, i.e., only encapsulant and MRI agent.

In addition to the three agents mentioned above, one, two, or three or more agents can be attached to the encapsulant directly or indirectly. For example, a PET (e.g., $^{18}F$, $^{64}Cu$, $^{11}C$, $^{13}N$, $^{15}O$, and the like), SPECT (e.g., $^{99}Tc$, $^{67}Ga$, $^{192}Iridium$ and the like), fluorochrome (e.g., Alexa 647, Alexa 488 and the like), radio nucleotide (e.g., alpha-emitting radionuclides (e.g., At-211, Bi-212, Bi-213, Ra-223, and Ac-225), beta-emitting radionuclides (e.g., Cu-67, Y-90, Ag-111, I-131, Pm-149, Sm-153, Ho-166, Lu-177, Re-186, and Re-188)), and the like, can be added to the probe and be detected using appropriate detection systems. In addition, the use of a radionuclide can be used to induce signal via Cherenkov radiation.

Furthermore, the probe can include a targeting agent (e.g., a chemical or biological agent) having an affinity for a target in the living host, where the agent is disposed indirectly or directly on the encapsulant. In particular, the probe can include, but is not limited to, a drug, a therapeutic agent, a radiological agent, a chemological agent, a small molecule drug, a biological agent (e.g., peptides, proteins, antibodies, antigens, and the like) and combinations thereof, that can be used to image, detect, study, monitor, evaluate, and/or screen a disease, condition, or related biological event corresponding to the target. It should be noted that a probe modified by conjugation to other molecules (e.g., proteins, peptides, small molecules, and the like) in order to target the probe to a particular molecular target are intended to be covered by embodiments of the present disclosure.

In an embodiment, the targeting agent can function to cause the probe to interact with a molecule(s). In an embodiment, the targeting agent can have an affinity for a cell, a tissue, a protein, DNA, RNA, an antibody, an antigen, and the like, that may be associated with a condition, disease, or related biological event, of interest. In particular, the targeting agent can function to target specific DNA, RNA, and/or proteins of interest. In an embodiment, the targeting agent can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, or combinations thereof, that have an affinity for a condition, disease, or related biological event or other chemical, biochemical, and/or biological events of the condition, disease, or biological event. In an embodiment, the targeting agent can include: sequence-specific DNA oligonucleotides, locked nucleic acids (LNA), and peptide nucleic acids (PNA), antibodies, and small molecule protein receptors.

Embodiments of the present disclosure include probes that can be used to image, detect, study, monitor, evaluate, and/or screen a sample or subject (e.g., whole-body or a portion thereof). Embodiments of the present disclosure include a method of planning resection of a brain tumor, evaluating a brain tumor, intraoperative tumor resection guidance, verification of clean margins in vivo or ex vivo, or the like. In an embodiment, the method can include a pre-operative and intra-operative procedure time frame and can also include the post-operative procedure time frame to study removed tissue. In an embodiment, the method can include administering an appropriate amount of a probe (e.g., an effective dose(s)) so that the probe is detectable in the brain tumor for a few days to a week or ten days. If needed, larger doses can be administered to maintain a detectable amount of the probe in the brain tumor. In addition, multiple doses of the probe can be administered during the time frame of the procedure.

Now referring to methods of evaluating a brain tumor, after the probe has been administered to the subject, the following can be obtained during one or more of the pre-operative, intra-operative, and/or post-operative time frames of the procedure: a MRI signal, a photoacoustic signal, and a Raman signal. Each of the signals can be included in an information set (e.g., signal, location of the signal, time of the signal, intensity of the signal, and the like, wherein one or more of these or a combination can be referred to as "data" as discussed below) that can be analyzed. An appropriate energy can be used to produce the photoacoustic and Raman signals, as described in more detail in the Examples.

In an embodiment, the MRI signal can be used to produce an image corresponding to one or more of: the localization of the whole brain tumor, macroscopic delineation of the whole brain tumor, and residual portions of the brain tumor. The first two can be measured or detected during the pre-operative time frame of the procedure, while the last is measured or detected during the post-operative time frame of the procedure. The MRI signal can be measured or detected using an MRI system such as 15T, 11T, 9.4T, 7T, 3T, 1.5T, or 0.5T or less, which is well known in the art. Additional details are provided in the Examples.

In an embodiment, the photoacoustic signal is used to produce an image corresponding to the brain tumor with deep tissue penetration (e.g., about 4 to 10 cm). The photoacoustic signal can be measured using a photoacoustic system as described herein. Additional details are provided in the Examples.

In an embodiment, the Raman vibrational signal can be used as a guide to defining the brain tumor margins as well as produce an image of a portion of the brain (e.g., edges of transition from tumor to brain tissue). The Raman vibrational signal can be measured using a Raman system as described herein (e.g., raster scanning or point by point scanning). Additional details are provided in the Examples.

In an embodiment, the MRI signal, the photoacoustic signal, and the Raman signal (or the corresponding information set), can be used to image and/or determine the location, relative position, and/or the presence of the probe at a particular location, of one or more of: the brain tumor and the brain tumor margins, during the operative procedure. The signals (or the corresponding information set) can be used alone or in combination at any given point during the procedure. The signals (or the corresponding information set) can all be used to facilitate a superior resection procedure since at certain points of the procedure a single type of probe can be used to obtain each type of signal. This is advantageous because repeated injection of contrast agents can show decreased efficacy and may induce toxicity.

Now referring to methods of planning resection of a brain tumor, after the probe has been administered to the subject, the following can be obtained during one or more of the pre-operative, intra-operative, and/or post-operative time frames of the procedure: MRI data, photoacoustic data, and Raman data. The data can be obtained by appropriate processing of the each type of signal received to produce an image or monitored although not processed into an image. In an embodiment the one or more types data can be used to visualize (e.g., image) the brain tumor. Two or more of the types of data can be combined to visualize (e.g., produce an image) of the brain tumor. Processing of the signals to produce data is discussed in the Examples and also may be known in the art (e.g., MRI data processing).

In an embodiment, the MRI data corresponds to one or more of: brain tumor localization and macroscopic delineation of the brain tumor. In an embodiment, the MRI data can be used to obtain the whole brain tumor in the pre-operative time frame as well as obtain intra-operative or post-operative data regarding any remaining brain tumor. Additional details are provided in the Examples.

In an embodiment, the photoacoustic data corresponds to the brain tumor with deep tissue penetration (e.g., about 5 to 10 cm deep into the subject). In an embodiment, the photoacoustic data corresponds to the intra-operative time frame of the procedure. Additional details are provided in the Examples.

In an embodiment, the Raman data corresponds to the brain tumor margins. In an embodiment, the Raman data corresponds to the intra-operative time frame of the procedure and can also be used in the post-operative time frame of the procedure. Additional details are provided in the Examples.

In an embodiment, the MRI data, photoacoustic data, and the Raman data can be used to determine the location of one or more of: the brain tumor and the brain tumor margins, during an operative procedure. The data can be used alone or in combination at any given point during the procedure. The data can all be used to facilitate a superior resection procedure since at certain points of the procedure a single type of probe can be used to obtain each type of data. This is advantageous because each of the three modalities has complementary strengths such as greater depth penetration, greater spatial resolution, greater sensitivity, and greater specificity.

Although the methods described above are directed to brain tumors, other tissue types can be substituted for the brain tumor. For example, pre-cancerous can cancer can be considered in the same way. In some embodiments, a targeting agent may need to be added to the probe for the probe to be disposed in the pre-cancerous or cancerous cells. As discussed in the Examples, no targeting agent is needed since the probe in the Example becomes disposed in the brain tumor without a targeting agent. Additional details are described in the Examples.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction:

The vexing difficulty in delineating brain tumor margins represents a major obstacle toward better outcome of brain tumor patients. Current imaging methods are often limited by inadequate sensitivity, specificity, and spatial resolution. Here we show that a unique triple-modality Magnetic resonance imaging-Photoacoustic imaging-Raman imaging nanoparticle (MPR) can accurately help delineate the margins of brain tumors in living mice both pre- and intra-operatively. The MPRs were detected by all three modalities with at least picomolar sensitivity both in vitro and in living mice. Intravenous injection of MPRs into glioblastoma-bearing mice led to specific MPR accumulation and retention by the tumors, allowing for non-invasive tumor delineation by all three modalities through the intact skull. Raman imaging allowed guidance of intra-operative tumor resection, and histological correlation validated that Raman imaging is accurately delineating brain tumor margins. This novel triple-modality nanoparticle approach holds promise to enable more accurate brain tumor imaging and resection.

Introduction:

The completeness of the surgical resection is an important factor for the prognosis of brain tumor patients[1,2]. In trying to achieve more complete glioma resections, the surgeon encounters several hurdles, which include irregular and indistinct tumor margins as well as tumor growth adjacent to or invading crucial neurological structures[3]. A wide variety of techniques have been explored to date in an effort to better visualize tumor margins. For instance, pre-operative magnetic resonance imaging (MRI) has been used to guide stereotactic surgery, where the MR images are used to determine the macroscopic outline of the tumor[4]. However, such methods suffer from limited spatial resolution and incongruencies between pre-operative MRI and actual tumor borders during surgery due to brain shift[5]. Intra-operative MRI usually requires the administration of gadolinium (Gd)-chelates, which suffer from short blood half-life requiring repeated injections[6], high dosages[7] and inaccuracies due to surgically induced false-positive contrast enhancement[8]. Several intra-operative optical methods have been suggested, either based on intrinsic tissue optical properties[3,9] or exogenous contrast agents[10-12]. However, these optical techniques suffer from poor specificity due to tissue autofluorescence, limited resolution and depth of penetration, which ultimately limit localization of the true brain tumor margins[13,14].

Photoacoustic imaging is a novel technology that largely overcomes the depth and resolution limits of optical imaging. In Photoacoustic imaging, light pulses excite target molecular imaging agents causing very slight heat production. This produces ultrasound waves that are recorded by an ultrasound transducer leading to a three-dimensional image of the imaging agent distribution in living subjects[15,16]. Raman imaging, another promising and complementary optical imaging technique, can be greatly enhanced by the Surface Enhanced Raman Scattering (SERS) effect[17]. Due to the unique signature of the SERS spectrum, Raman imaging allows for highly specific and sensitive detection of SERS contrast agents as well as the multiplexing of multiple agents in living subjects[17-20].

An ideal molecular imaging agent would be 1) sequestered and retained by a tumor for a long enough period such that a single injection of the agent would facilitate 2) both pre- and intra-operative imaging allowing for respective pre-operative planning and intra-operative resection of the tumor. It should also allow for both 3) deep tumor visualization and 4) highly sensitive and specific detection of tumor margins.

Here we present a novel approach that attempts to fulfill these criteria. We have designed and tested MPRs for a triple-modality strategy that, to our knowledge, is the first to allow combined MRI, Photoacoustic imaging and Raman imaging. After a single tail-vein injection into orthotopic mouse glioblastoma models, the MPRs accumulated in the tumor but not in healthy brain tissue due to the enhanced permeability and retention (EPR) effect[21] (FIG. 1.1). The particles resided in the tumor for an extended period of time 1 week) and were detected with all three modalities in living mice with at least picomolar sensitivity. This allowed 1) whole brain tumor localization for pre- and intra-operative macroscopic delineation using MRI, 2) high spatial resolution, three-dimensional imaging using Photoacoustic imaging, and 3) high sensitivity, high specificity and high resolution surface imaging of tumor margins using Raman imaging. Moreover, excised tissues may be further analyzed post-operatively using Raman imaging to confirm clear margins (FIG. 1.1).

Results

Synthesis and Characterization of Triple-modality MPRs:

The MPR nanoparticle is composed of a 60 nm gold core covered with the Raman molecular tag, trans-1,2-bis(4-pyridyl)-ethylene. This thin Raman-active layer is further protected by a 30 nm silica coating. We further modified the particles with DOTA-$Gd^{3+}$ via a maleimide linkage (see Methods), resulting in a gold-silica-based SERS nanoparticle coated with $Gd^{3+}$ ions (MPR) (FIG. 1.2a,1.2 b). We determined the number of $Gd^{3+}$ ions per MPR to be 79,340±2,270 via inductively coupled plasma atomic emission spectroscopy (ICP-AES). A portion of these $Gd^{3+}$ ions could be bound directly to the silica surface. To test the serum stability of the MPRs we performed ICP-AES and found that the number of $Gd^{3+}$ ions per MPR did not significantly decrease in the presence of serum after 2 h or 24 h of incubation (data not shown). In addition, we validated that the MPRs are stable in serum by measuring their optical stability (FIG. 1.6) and hydrodynamic size distribution (FIG. 1.7) over a course of 24 h of incubation in mouse serum. The stable binding of $Gd^{3+}$ ions to the nanoparticle surface and absence of any free $Gd^{3+}$ ions in solution was verified by acquiring T1-weighted MR images of the supernatant after particle centrifugation (data not shown). The MPRs demonstrated a very high T1 relaxivity of $3.0 \times 10^6$ $mM^{-1} s^{-1}$ (in $H_2O$, at a field strength of 7 T and 20° C.), with minimal batch-to-batch variation (see error bars in FIG. 2c). The MPR optical absorbance peaked at 540 nm, with a very high absorbance coefficient of $2.75 \times 10^{10}$ $cm^{-1} M^{-1}$ (FIG. 1.2d). We therefore further modified our custom-made Photoacoustic imaging system to include a 532 nm laser to allow imaging of the MPRs (see Supplementary Methods). The MPRs demonstrated a unique Raman signature (FIG. 1.2e), which was identical before and after the surface conjugation of the maleimide-DOTA-Gd to the particle (FIG. 1.8). To test for possible photobleaching, we irradiated the MPRs in both the Photoacoustic and Raman imaging systems. During 30 min of continuous laser irradiation, the optical absorption and Raman signal did not vary more than 2% each (FIG. 1.2f, 1.2g, and Supplementary Methods).

In vitro and In vivo Detection of MPRs by MR, Photoacoustic and Raman Imaging:

Next, we determined the in vitro detection threshold of the MPRs for each modality. An agarose phantom containing MPRs in concentrations ranging from 1.22 pM to 1250 pM (n=3 per concentration) was imaged with MRI, Photoacoustic and Raman (FIG. 1.9a), and signal intensities were determined by region of interest (ROI) analysis (FIG. 1.9b). The lowest detectable concentrations were 4.88 pM for MRI, 1.22 pM for Photoacoustic, and 610 fM for Raman imaging (see FIG. 1.10). The MRI, Photoacoustic and Raman signals produced by MPRs in vitro were highly correlated to the MPR concentration (P<0.0001 for all modalities, with $R^2$=0.99, 0.99 and 0.97, respectively) (FIG. 1.9b) and were further highly linear and correlated to each other (see FIG. 1.16). For a comparison of the depth of penetration of Photoacoustic imaging versus Raman imaging, see FIG. 1.17.

We then measured the detection threshold of the MPRs in living mice. All animal experiments were performed in compliance with the Guidelines for the Care and Use of Research Animals established by the Stanford University Animal Studies Committee. MPRs diluted in matrigel to six different concentrations (range 50 pM to 1100 pM) were injected subcutaneously in the right flank of nude mice (n=3) and scanned in the MRI, Photoacoustic and Raman systems (FIG. 1.18a). The MRI, Photoacoustic and Raman signals in vivo highly correlated to the MPR concentration (P=0.001 for all modalities, with $R^2$=0.99, 0.97 and 0.99, respectively) (FIG. 1.18b). Due to the high background signal, the sensitivity of MRI and Photoacoustic imaging was limited by the tissue background signal. For both MRI and Photoacoustic imaging, 50 pM of MPRs gave the equivalent signal as muscle. Raman imaging, however, had negligible tissue background signal, and was therefore limited only by the signal-to-noise ratio. Indeed, at the nominal concentration of 50 pM, the Raman image clearly visualized the MPRs. This explains why the Raman response had the steepest slope in vivo compared to MRI and Photoacoustic imaging (P<0.0001 compared to either MRI or Photoacoustic imaging; however, the slope of Photoacoustic imaging was not statistically different from the MRI slope, P=0.16), whereas in vitro, where no significant background signal is present, Photoacoustic imaging has the steepest slope. Finally, a linear correlation between the signals of the three modalities was observed (FIG. 1.19).

MPRs Allow Triple-modality Brain Tumor Visualization in Intact Living Mice:

We next aimed at determining whether the MPRs could be used for orthotopic brain tumor detection in living mice. We hypothesized that in an orthotopic glioblastoma brain tumor model the nanoparticle probe would enter the extravascular space due to diffusion through the disrupted blood-brain-barrier and accumulate in cells within the tumor without necessitating a specific targeting mechanism (EPR effect), as previously observed for iron oxide nanoparticles[22]. We used an orthotopic brain tumor model where enhanced green fluorescent protein (eGFP)-transfected human gliomablastoma cells (eGFP+U87MG) were implanted via a stereotactic implantation device into the striatum of nude mice (Supplementary Methods). We injected tumor-bearing mice (n=4) via tail-vein with MPRs and performed consecutive Photoacoustic, Raman and MR imaging on each animal pre-injection and at 2 h, 3 h and 4 h post-injection, respectively (FIG. 1.3; FIG. 1.20).

The post-injection images demonstrated clear visualization of the tumor with all three modalities, despite being acquired through intact skin and skull (FIG. 1.3a). The Photoacoustic and Raman images were co-registered with the MRI image, demonstrating good co-localization between the three modalities (FIG. 1.3a). In parallel to the Photoacoustic images of the brain, we also acquired co-registered ultrasound images in order to register the Photoacoustic images to the MR images in orthogonal planes (FIG. 1.3b) (using Amide[23] and Amira software, see Supplementary Methods).

ROI quantification of the signal in the tumor shows a significant increase in MRI, Photoacoustic and Raman signals after the tail-vein injection versus before (FIG. 1.3c). The MRI contrast-to-noise ratio (CNR) increased from 2.2±0.3 to 14.0±1.9 (mean±S.E.) (P=0.001). The Photoacoustic signal increased by 75% from 0.57±0.02 to 1.0±0.08 (arbitrary units (AU)) (P=0.001). The Raman system recorded zero signal before the injection, and an intense Raman signal of 1.0±0.09 (AU) (P=0.012) after injection.

We then determined the molecular imaging agent kinetics with all three modalities using additional orthotopic eGFP+ U87MG tumor-bearing mice (n=4 each for MRI and Raman imaging; the Photoacoustic data was derived from the first set of mice described in FIG. 1.3). We analyzed the signal kinetics for each of the mice individually in the MRI, Photoacoustic and Raman imaging systems (FIG. 1.16). We acquired data before injection and at 0.5 h, 1 h, 1.5 h and 2 h post-injection. For MRI, an additional 24 h time point was acquired. The signal was observed to increase markedly between the pre-injection and the 30 min post-injection time points in all three modalities (from 1.4±0.24 to 8.7±0.76 CNR for MRI (P<0.001), 60±14% increase for Photoacoustic imaging (P<0.01), and from zero to 1.96±0.27 (AU) for Raman imaging (P<0.001). The signal then reached a plateau for MRI and Photoacoustic, remaining essentially stable up to the latest examined time point of 2 h (24 h for MRI). Of note, this behavior contrasts with conventional clinically used Gd-based contrast agents, which demonstrate rapid washout within minutes after injection, while the MPRs demonstrate persistent signal enhancement (FIG. 1.16). For Raman, an initial signal peak was observed, before a plateau was reached (P<0.0001). This effect is presumed due to initial nonspecific circulation of MPRs in superficial layers (e.g. skin), to which Raman is most sensitive (FIG. 1.16).

Histological Validation of MPR Sequestration by Brain Tumors:

We next examined the distribution of the MPRs within the brain by histology. We performed immunohistochemistry with antibody staining against eGFP and CD11b to visualize eGFP+U87MG tumor cells and microglia, respectively. In particular, we sampled sections including the interface between tumor and surrounding brain tissue. We then examined adjacent sections with high-resolution Raman microscopy (Supplementary Methods) and correlated these images with the immunohistochemistry results. We observed a strong Raman signal within the tumors, but not in healthy brain tissue, with very good delineation of the actual tumor border by the Raman signal (FIG. 1.4). Scanning transmission electron microscopy (STEM) (FIG. 1.4) further corroborated these results, finding numerous MPRs in tumor sections, while none were found in surrounding brain tissue (923 MPRs found in tumor in an examined volume of 57,500 $\mu m^3$ (average of 0.016 nanoparticles/$\mu m^3$), 0 nanoparticles found in healthy brain in an examined volume of 12,500 $\mu m^3$).

To further examine the ability of the MPRs to visualize not only the bulk tumor, but also invasive tumor margins, we used an orthotopic primary human xenograft glioblastoma mouse model (TS543 cell line[24] grown as neurospheres). As confirmed by correlative Raman microscopy, immunohistochemistry, and scanning electron microscopy (SEM), the MPRs accumulated in infiltrating tumor margins (FIG. 1.17). In addition, Raman imaging was able to depict finger-like tumor protrusions and even isolated microscopic tumor foci (FIG. 1.18).

MPRs Guide Brain Tumor Resection In vivo:

Finally, we explored whether tumor resection along the Photoacoustic and Raman signals, 24 h after intravenous injection of MPRs, could facilitate tumor resection. Initially, we tested the ability of Photoacoustic imaging to delineate brain tumors in situ, which demonstrated a reduced signal in the resected area (FIG. 1.19). Next, we placed brain tumor-bearing mice (n=3) under general anesthesia and performed craniotomies and subsequent in vivo Raman imaging. Sections of the brain tumors were then removed using visual inspection. High-resolution intra-operative Raman images after each resection step were obtained and correlated with intra-operative photographs. The whole tumor was visualized with Raman imaging (first image in FIG. 1.5a,b). With sequential resection steps, a high congruency between residual tumor tissue (FIG. 1.5a) and presence of Raman signal (FIG. 1.5b) was noted, and vice versa between resected tumor and lack of Raman signal. Of note, after the tumor resection appeared complete using visual inspection, several small foci of residual Raman signal (dashed box in FIG. 1.5b) were noted in the resection bed. When we then extended the resection to include these foci located near the tumor-brain interface and histologically analyzed this tissue, we found frequent finger-like microscopic extensions of tumor into the surrounding brain tissue (FIG. 1.5c). These cancerous foci, which were otherwise not visible by the naked eye, were detected due to the specific accumulation of the MPRs therein.

Discussion

We designed and tested a unique triple-modality nanoparticle that is, to our knowledge, the first to allow combined MRI, Photoacoustic and Raman imaging. The MPRs described here could enable radiologists and neurosurgeons to "see" the same probe before and during surgery, thus allowing more accurate brain tumor resection by exploiting the complementary strengths of each modality.

The excellent MRI detectability of the MPRs in the picomolar range is a direct result of their very high longitudinal relaxivity of $3.0 \times 10^6$ mM$^{-1}$ s$^{-1}$. To our knowledge, this represents the highest relaxivity of a nanoparticle reported to date.

The second modality, Photoacoustic imaging, is a relatively new technique that allows deeper tissues to be imaged with higher spatial resolution compared to most optical techniques[25-27]. The exceptionally high optical absorbance coefficient of the MPRs is over 200-fold higher than, for example, previously reported Photoacoustic imaging agents based on carbon nanotubes[28,29]. In conjunction with its three-dimensional capabilities, Photoacoustic imaging could guide the more gross resection steps and even identify tumor tissue residing under the surface of normal brain tissue. Then, to completely remove microscopic tumor deposits, Raman imaging with its superior sensitivity could be employed.

Raman spectroscopy in conjunction with MPRs offers ultrahigh sensitivity in the picomolar range as opposed to the nanomolar sensitivity achievable with fluorescence imaging of quantum dots[13,17,18,20]. Raman imaging of MPRs, in contrast to other optical imaging techniques, does not suffer from autofluorescence or background signal because the MPR spectral signature is highly amplified and unique ("fingerprint"). While the main limitation of Raman imaging is its limited penetration depth, tumor visualization was achieved in our study through the intact skin and skull in live mice (depth of 2-5 mm). This result is a combination of the design of the nanoparticle with its gold core producing a surface plasmon resonance for Raman signal enhancement; the Raman substrate used; and the number of nanoparticles accumulating within the tumor. Raman nanoparticles are inherently insensitive to photodestruction, which represents a known problem of organic fluorochromes. Furthermore, unlike most quantum dots, which are cytotoxic[30,31], MPR nanoparticles are based on inert gold and silica and thus may have a better chance for clinical translation. Gold and gold-silica nanoparticles have excellent cytotoxicity profiles, as illustrated by detailed toxicity studies in animals[32-34] and several clinical trials[21]. The design of the MPRs would also allow for multiplexing[20] with the potential to detect multiple biomarkers simultaneously in vivo.

In addition, MPRs have a unique advantage over conventional low molecular weight contrast agents. For example, low molecular weight Gd-chelates or fluorochromes accumulate in the extracellular space, where blood-brain-barrier breakdown has occurred, and then undergo both rapid diffusion through the interstitium and renal clearance. These low molecular weight agents are therefore unable to delineate tumors for the time period spanning the resection procedure, let alone for the entire period between pre-operative planning and surgical intervention. This diffusion process also introduces imprecision of probe localization, requires repeated contrast administration (e.g., Gd-chelates during intra-operative MRI), and can cause false positive results due to surgically induced contrast enhancement. In contrast, the in vivo kinetic studies performed with the MPRs here demonstrate that the particle is being retained in the tumor, allowing repeated imaging as required without the need for repeated injection. This contrast agent behavior may also be useful for distinguishing tumor recurrence from non-specific treatment-related effects. As the MPR approach relies on the EPR effect, it could potentially be applied to image other cancer types with intrinsic EPR effect including: lung cancer, melanoma, renal cancer, hepatoma, and many others[35]. Finally, the long intratumoral retention of the MPRs could also be exploited for drug delivery or photothermal therapy.

Novel instrumentation, including endoscopic and intra-operative Photoacoustic and Raman imaging devices required for clinical translation of the MPR approach, are currently under development[36,37]. Ideally, a combination of both devices integrated in one handheld probe would be desirable in the operating room. In particular, such endoscopes should be designed for easy intra-operative navigation and enable real-time imaging. Further development of instrumentation could lead to improved brain tumor surgery and patient outcome in the future. For additional discussion, please refer to the Supplementary Discussion below.

Methods

Particle Synthesis

Reagents. SERS nanotags (Cabot Security Materials, Inc.) comprised a 60 nm diameter gold core coated with a monolayer of a Raman-active organic molecule, trans-1,2-bis(4-pyridyl)-ethylene, and encapsulated with a 30 nm diameter silica shell, making the entire particle on the order of ~120 nm. We purchased phosphate buffered saline, 2-(N-morpholino)ethanesulfonic acid (MES), 3-mercaptopropyl-trimethoxysilane (MPTMS), gadolinium chloride hexahydrate, and sodium chloride from Sigma-Aldrich, 5,5'-dithio-bis(2-nitrobenzoic acid) (DTNB, Ellman's reagent) from Pierce and 1,4,7,10-tetraazacyclododecane-1,4,7-tris-acetic acid-10-maleimidoethylacetamide (maleimide-DOTA) from Macrocyclics.

Bioconjugation. We activated the SERS nanotag surface with 10 mM MES buffer of pH 7.0 for binding of maleimide-DOTA to the mercaptopropyl trimethoxysilane (MPTMS)-coated surface. We added the DOTA chelator at a molar excess of $7.5 \times 10^5$ per nanoparticle from a stock solution of 1 mg/mL, reacted for 2 h at room temperature (RT) and removed excess reagent via centrifugation (5,000 g×5 min)× 3. We added gadolinium chloride hexahydrate (3 mg/mL) to the DOTA-activated nanoparticles in MES buffer (pH 6.25), with a ratio of Gd to nanoparticle of $7.5 \times 10^5$:1. We heated this solution to 50° C. for 2 h, washed ×3 as above, and then purified by dialysis versus distilled water and a 3.5 kDa molecular weight cutoff membrane. Optical absorbance was measured using a UV-Vis spectrophotometer (DU-640 spectrophotometer, Beckman Coulter).

MRI:

We conducted MRI scans with a dedicated small animal MRI scanner, custom-designed pulse sequences and radiofrequency (RF) coils. The small animal scanner consisted of a scientific superconducting magnet (Magnex) with 7.0 Tesla (T) field strength, gradient (Resonance Research, Inc.) with clear bore size of 9 cm, maximum gradient amplitude of 770 mT/m and maximum slew rate of 2,500 T/m/s and a General Electric (GE) console and Copley 266 amplifiers.

We obtained T1-weighted fast spin echo sequences (TE/TR 7.7 ms/800 ms) using 5NEX, a 256×256 matrix, a 3.0 cm field-of-view (resulting in an in-plane resolution of 117 µm), a slice thickness of 700 µm and a total imaging time of ~4 min. For acquisition of T1 maps, we used an inversion recovery sequence (TE/TR 7.7 ms / 5,000 ms) with inversion times of 50, 100, 200, 500, 800, 1200 and 2100 ms. We obtained estimates of T1 relaxation times by fitting the acquired inversion recovery images to a function of the form $$S = M_0 \left| 1 - 2e^{\frac{TI}{T1}} + e^{\frac{TR}{T1}} \right|$$

(Reference [38]). We performed data fitting using a non-linear least squares algorithm implemented in the RT_Image[39] analysis software. We obtained T2-weighted fast spin echo sequences (TE/TR 71 ms/4,000 ms) using 4 NEX, a 256×128 matrix, a 3.0 cm field-of-view, a slice thickness of 700 µm and a total imaging time of ~3.5 min.

Raman Imaging of Living Mice:

To measure Raman signal, we used a customized Raman microscope (InVia, Renishaw). Since previous reports[18,20], we further customized the microscope by integrating a 785 nm point source laser, piezo-controlled stage for micron-resolved spatial mapping, and a 1 inch charge-coupled device detector for spectral resolution of 1.07 $cm^{-1}$. We carefully positioned living mice into a nose cone under the microscope and anesthetized with 2-3% isoflurane delivered by 100% oxygen as the carrier gas at 2 L/min through an isoflurane vaporizer. We used a semiconductor diode near-infrared laser operating at 785 nm as the excitation source with a laser power of ~20 mW measured at the skin surface. We obtained Raman images by using a Raman point mapping method. We used a computer-controlled x-y translation stage to raster-scan over the brain, using an integration time of 1-5 s, a 5× or 12× lens, a slit size of 400 µm, and either a 750 µm or 500 µm step size. Raman spectra were analyzed with Wire 2.0 Software (Renishaw) and Nanoplex-™SENSERSee software (provided by Cabot Security Materials, Inc.)

Photoacoustic Imaging System:

Our custom-built Photoacoustic system[15] is illustrated in FIG. 1.21. A tunable pulsed laser with a repetition rate of 10 Hz and a pulse width of 5 ns (Nd:YAG Surelight-III-10, Continuum) illuminates the object through a fiber optic ring light (50-1353 Ringlight, Fiberoptic Systems Inc.). The average energy density of the laser at 532 nm was ~8 $mJ/cm^2$ on the tissue surface, which is below the limitation for laser skin exposure defined by the American National Standards Institute[40]. We used a 5 MHz focused transducer (A309S-SU-F-24.5-MM-PTF; 25.5 mm focal length, 4 MHz bandwidth, f-number of 2.0, depth of focus of 6.5 mm, lateral resolution of 600 µm, and axial resolution of 380 µm; Panametrics-Olympus NDT) to acquire both pulse-echo and Photoacoustic images. In addition, we acquired high-resolution ultrasound images using a 25 MHz focused transducer (V324-SU-25.5-MM; 27 mm focal length, 12 MHz bandwidth, F number of 4.2, depth of focus of 7.5 mm, lateral resolution of 250 µm, and axial resolution of 124 µm; Panametrics-Olympus NDT).

REFERENCES, EACH OF WHICH IS INCORPORATED HEREIN BY REFERENCE

1. Bucci, M. K., et al. Near complete surgical resection predicts a favorable outcome in pediatric patients with nonbrainstem, malignant gliomas: results from a single center in the magnetic resonance imaging era. *Cancer* 101, 817-824 (2004).
2. Stupp, R., et al. Changing paradigms-an update on the multidisciplinary management of malignant glioma. *Oncologist* 11, 165-180 (2006).
3. Toms, S. A., et al. Intraoperative optical spectroscopy identifies infiltrating glioma margins with high sensitivity. *Neurosurgery* 57, 382-391; discussion 382-391 (2005).
4. Orringer, D. A., et al. The brain tumor window model: a combined cranial window and implanted glioma model for evaluating intraoperative contrast agents. *Neurosurgery* 66, 736-743 (2010).
5. Reinges, M. H., et al. Course of brain shift during microsurgical resection of supratentorial cerebral lesions: limits of conventional neuronavigation. *Acta Neurochir (Wien)* 146, 369-377; discussion 377 (2004).
6. Ludemann, L., Hamm, B. & Zimmer, C. Pharmacokinetic analysis of glioma compartments with dynamic Gd-DTPA-enhanced magnetic resonance imaging. *Magn Reson Imaging* 18, 1201-1214 (2000).
7. Knauth, M., Wirtz, C. R., Aras, N. & Sartor, K. Low-field interventional MRI in neurosurgery: finding the right dose of contrast medium. *Neuroradiology* 43, 254-258 (2001).
8. Knauth, M., et al. Surgically induced intracranial contrast enhancement: potential source of diagnostic error in intraoperative MR imaging. *AJNR Am J Neuroradiol* 20, 1547-1553 (1999).
9. Beljebbar, A., Dukic, S., Amharref, N. & Manfait, M. Ex vivo and in vivo diagnosis of C6 glioblastoma development by Raman spectroscopy coupled to a microprobe. *Anal Bioanal Chem* 398, 477-487 (2010).
10. Ozawa, T., et al. Bromophenol blue staining of tumors in a rat glioma model. *Neurosurgery* 57, 1041-1047; discussion 1041-1047 (2005).
11. Shinoda, J., et al. Fluorescence-guided resection of glioblastoma multiforme by using high-dose fluorescein sodium. Technical note. *J Neurosurg* 99, 597-603 (2003).

12. Stummer, W., et al. Fluorescence-guided surgery with 5-aminolevulinic acid for resection of malignant glioma: a randomised controlled multicentre phase III trial. *Lancet Oncol* 7, 392-401 (2006).
13. de la Zerda, A., et al. A comparison between time domain and spectral imaging systems for imaging quantum dots in small living animals. *Mol Imaging Biol* 12, 500-508 (2010).
14. Kantelhardt, S. R., et al. Multiphoton excitation fluorescence microscopy of 5-aminolevulinic acid induced fluorescence in experimental gliomas. *Lasers Surg Med* 40, 273-281 (2008).
15. de la Zerda, A., et al. Carbon nanotubes as photoacoustic molecular imaging agents in living mice. *Nat Nanotechnol* 3, 557-562 (2008).
16. Wang, L. V. Multiscale photoacoustic microscopy and computed tomography. *Nat Photonics* 3, 503-509 (2009).
17. Zavaleta, C. L., Kircher, M. F. & Gambhir, S. S. Raman's "Effect" on Molecular Imaging. *J Nucl Med* (2011).
18. Keren, S., et al. Noninvasive molecular imaging of small living subjects using Raman spectroscopy. *Proc Natl Acad Sci USA* 105, 5844-5849 (2008).
19. Zavaleta, C., et al. Noninvasive Raman spectroscopy in living mice for evaluation of tumor targeting with carbon nanotubes. *Nano Lett* 8, 2800-2805 (2008).
20. Zavaleta, C. L., et al. Multiplexed imaging of surface enhanced Raman scattering nanotags in living mice using noninvasive Raman spectroscopy. *Proc Natl Acad Sci USA* 106, 13511-13516 (2009).
21. Adiseshaiah, P. P., Hall, J. B. & McNeil, S. E. Nanomaterial standards for efficacy and toxicity assessment. *Wiley Interdiscip Rev Nanomed Nanobiotechnol* 2, 99-112 (2010).
22. Trehin, R., et al. Fluorescent nanoparticle uptake for brain tumor visualization. *Neoplasia* 8, 302-311 (2006).
23. Loening, A. M. & Gambhir, S. S. AMIDE: a free software tool for multimodality medical image analysis. *Mol Imaging* 2, 131-137 (2003).
24. Vivanco, I., et al. The phosphatase and tensin homolog regulates epidermal growth factor receptor (EGFR) inhibitor response by targeting EGFR for degradation. Proceedings of the National Academy of Sciences of the United States of America 107, 6459-6464 (2010).
25. Ermilov, S. A., et al. Laser optoacoustic imaging system for detection of breast cancer. *J Biomed Opt* 14, 024007 (2009).
26. Manohar, S., et al. Initial results of in vivo non-invasive cancer imaging in the human breast using near-infrared photoacoustics. *Opt Express* 15, 12277-12285 (2007).
27. de la Zerda, A., et al. Photoacoustic ocular imaging. *Optics letters* 35, 270-272 (2010).
28. de la Zerda, A., et al. Ultrahigh sensitivity carbon nanotube agents for photoacoustic molecular imaging in living mice. *Nano letters* 10, 2168-2172 (2010).
29. de la Zerda, A., Kim, J. W., Galanzha, E. I., Gambhir, S. S. & Zharov, V. P. Advanced contrast nanoagents for photoacoustic molecular imaging, cytometry, blood test and photothermal theranostics. *Contrast Media & Molecular Imaging* 6, 346-369 (2011).
30. Zuin, S., et al. Weight of Evidence approach for the relative hazard ranking of nanomaterials. *Nanotoxicology* (2010).
31. Kircher, M. F., Gambhir, S. S. & Grimm, J. Noninvasive cell-tracking methods. *Nat Rev Clin Oncol* (2011).
32. Thakor, A. S., et al. The fate and toxicity of Raman-active silica-gold nanoparticles in mice. *Sci Transl Med* 3, 79ra33 (2011).
33. Thakor, A. S., et al. Oxidative stress mediates the effects of Raman-active gold nanoparticles in human cells. *Small* 7, 126-136 (2011).
34. Zavaleta, C. L., et al. Preclinical Evaluation of Raman Nanoparticle Biodistribution for their Potential Use in Clinical Endoscopy Imaging. *Small* 7, 2232-2240 (2011).
35. Maeda, H., Wu, J., Sawa, T., Matsumura, Y. & Hori, K. Tumor vascular permeability and the EPR effect in macromolecular therapeutics: a review. *J Control Release* 65, 271-284 (2000).
36. Koljenovic, S., et al. Raman spectroscopic characterization of porcine brain tissue using a single fiber-optic probe. *Anal Chem* 79, 557-564 (2007).
37. Short, M. A., et al. Development and preliminary results of an endoscopic Raman probe for potential in vivo diagnosis of lung cancers. *Opt Lett* 33, 711-713 (2008).
38. Nishimura, D. G. *Principles of Magnetic Resonance Imaging*, (Lulu Publishers Raleigh, N.C., 1996).
39. Graves, E. E., Quon, A. & Loo, B. W., Jr. RT_Image: an open-source tool for investigating PET in radiation oncology. *Technol Cancer Res Treat* 6, 111-121 (2007).
40. American National Standards Institute, American national standard for the safe use of lasers, *ANSI Standard* Z136.1-2000, ANSI, Inc., New York. (2000).

Supplemental Information for Example 1:
Supplementary Data
Serum Stability of Photoacoustic Signal To verify the stability of the optical absorbance of the MPRs in serum, MPRs were added to 50% mouse serum/50% PBS (total volume 1 mL, MPR concentration 13 pM). We monitored the optical absorbance of the solution at 532 nm at multiple time points for 22 h (FIG. 1.6). Control solution included 50% serum only. The optical absorbance of the control serum vial had increased slightly over the 22 h, likely due to the evaporation of water from the vial, leading to higher concentration of the serum. This effect has likely also occurred in the vial containing the MPRs in serum. However, subtracting the "serum only" absorbance from the "MPR in serum" absorbance shows a stable and consistent absorbance curve with a standard deviation from the mean average absorbance of 9.5%.

Stability of the Hydrodynamic Size During Serum Incubation

To validate the stability of the MPRs in serum, we measured the MPR's hydrodynamic size distribution using a dynamic light scattering instrument (Zetasizer, Malvern). The MPRs were added to 50% mouse serum/50% PBS at a concentration of 0.068 nM and incubated at 37° C. for 24 h. The sample was analyzed at 0 h, 1 h, 2 h, 4 h, 6 h and 24 h post-incubation by dynamic light scattering. Over the course of 24 h, we noticed a slight increase in the hydrodynamic radius and the polydispersity index (PDI) of the MPRs (peaking at 1 h post-incubation with serum), which is attributed to association with blood proteins. In addition, a small peak was observed near 4,500 nm, attributed to aggregation; however, this peak was less than 5% of the total intensity for all measurements. Hence, we concluded that the MPRs are stable in serum (FIG. 1.7).

Stability of Raman Spectrum Before vs. After Maleimide-DOTA-Gd Conjugation

We validated that the Raman spectrum of the MPRs is not affected by the surface conjugation procedure by acquiring the Raman spectrum of a sample before and after the conjugation with maleimide-DOTA-Gd. As illustrated in FIG. 1.8, the addition of maleimide-DOTA-Gd shows a negligible effect on the Raman spectrum.

Raman Ex Vivo Detection Threshold

The phantom depicted in Supplementary FIG. 1.9 was extended to include lower concentrations in order to determine the true Raman detection threshold (FIG. 1.10). The detection threshold for Raman imaging in this new agarose phantom was determined to be approximately 610 fM.

Correlation of Signal-concentration Curves for MRI vs. Photoacoustic vs. Raman Imaging (in Phantom)

We further explored the correlation between the MRI signal-concentration response curve to the Photoacoustic signal-concentration response curve, to the Raman signal-concentration response curve in the phantom experiment (FIG. 1.9). For this purpose, we plotted 3 graphs: MRI vs. Photoacoustic, MRI vs. Raman and Raman vs. Photoacoustic (FIG. 1.11).

Comparison of Depth Penetration—Photoacoustic Versus Raman Imaging

In order to compare the depth of penetration achieved by Photoacoustic imaging versus Raman imaging, we constructed a tissue-mimicking phantom containing MPRs at increasing depths. The phantom was based on an agarose gel to mimic the acoustic properties of soft tissues. India ink and liposyn were further added to the liquid agarose to mimic the optical absorption and optical scattering properties of biological tissues (see Supplementary Methods). The depths in the phantom were measured by an independent ultrasound image of the phantom which showed the location of the inclusions with respect to the upper surface of the phantom.

As FIG. 1.12 shows, Photoacoustic imaging was able to detect signal from all wells of the phantom, i.e. depth of penetration is well beyond 7.1 mm. The deepest well Raman imaging was capable of visualizing was 4.5 mm in depth.

These results are highly dependent on the specific tissue optical properties (scattering and absorption alike). Specifically, white and gray matter exhibit different optical properties, which influence the depth of penetration. Hence, the values calculated here should only be interpreted as guidelines for relative rather than absolute penetration depth values.

Correlation of Signal-concentration Curves for MRI vs. Photoacoustic vs. Raman Imaging (In vivo)

We then explored the correlation between the MRI signal-concentration response curve to the Photoacoustic signal-concentration response curve, to the Raman signal-concentration response curve in the in vivo subcutaneous injection experiment (FIG. 1.13). A high degree of linearity was observed across all three modalities (FIG. 1.14).

Dynamic Triple-modality Imaging

In order to determine the kinetics of the MPRs in all three modalities, we prepared additional eGFP$^+$U87MG orthotopic tumor-bearing mice (n=4 for MRI and n=4 for Raman imaging. The data for Photoacoustic imaging is derived from the same mice (n=4) described in FIG. 3 of the main text. A dose of 170 µL of 16 nM MPR suspension was injected intravenously into mice, and MRI, Photoacoustic, or Raman images were taken before the injection as well as 30 min, 60 min, 90 min and 120 min post-injection without moving the mice from the respective imaging instrument. The mice that were scanned using MRI underwent an additional 24 h post-injection MRI scan. As shown in FIG. 1.16, the MRI tumor contrast-to-noise ratio has increased significantly by 30 min post-injection and remained high throughout the 24 h period. The kinetics of the MPRs that were observed with the Photoacoustic system were very similar to that of MRI, further validating this behavior. Finally, the Raman signal showed a significant increase 30 min post-injection, and then dropped and stabilized at about half the value (FIG. 1.16). This behavior can be explained by the fact that Raman imaging, unlike MRI or Photoacoustic imaging, is integrating the signal from all tissues under the surface into a 2D image. This includes the skin and healthy brain tissue in which the MPRs circulate but are not retained.

Visualization of Infiltrative Tumor Margins, Finger-like Protrusions, and Isolated Tumor Foci FIG. 1.17 illustrates MPRs that accumulate in infiltrating tumor margins in an orthotopic primary human glioblastoma (GBM) xenograft mouse model.

FIG. 1.18 illustrates MPRs to visualize finger-like protrusions and isolated foci in an orthotopic primary human glioblastoma (GBM) xenograft mouse model.

Intra-operative Photoacoustic Imaging

In addition to the Raman intra-operative experiment (FIG. 1.10), we have demonstrated that Photoacoustic imaging can further be used to complement Raman imaging in intra-operative guidance of tumor resection. A mouse bearing a glioblastoma tumor (primary human xenograft) was injected with MPRs (150 µl, 16 nM). 24 h post-injection, the mouse was perfused with PBS, sacrificed and the brain excised and embedded in agarose. Photoacoustic images were acquired before and after partial tumor resection (FIG. 1.19). An absence of Photoacoustic signal in the resected portion of the tumor was observed, while a residual Photoacoustic signal was observed from the non-resected tumor. This experiment provides preliminary demonstration that the Photoacoustic tomographic information further complements the two-dimensional Raman image, as it provides the surgeon with depth-information on the area that should be resected.

B. Supplementary Discussion

As many disease states do not exhibit an intrinsic Photoacoustic contrast, it is necessary to administer a Photoacoustic contrast agent. The nanoparticle used here with its 60 nm diameter gold core was shown to exhibit the highest Photoacoustic signal reported to our knowledge (e.g., 4.500-fold higher than carbon nanotubes[1] and ~ten-fold higher than most gold nanorods[2]). While other Photoacoustic contrast agents may exhibit lower absolute Photoacoustic signal, some were reported to have peak absorption in the near infra-red[2-5], where tissue background signal is reduced. However, targeting them to tumors has been proven to be highly challenging[2-6]. In fact, apart from this current work, we are not aware of any report where nanoparticles were shown to accumulate in deep tumors and produce a detectable Photoacoustic signal. Hence, while the peak Photoacoustic wavelength of the MPRs is in theory not optimal for tissue penetration, their very high optical absorbance at this wavelength compensates for this fact to some degree (see FIG. 1.20, showing 123-fold higher absorbance of MPR nanoparticles than gold nanorods (Nanorodz™ Nanopartz Inc., 10 nm diameter, 38 nm length; peak absorbance at 780 nm) at 532 nm and 2.5-fold higher absorbance than gold nanorods at 780 nm). While the exact depth of penetration achievable using the MPRs is not fully known in vivo, this parameter could be evaluated in future studies.

Another potential imaging modality that can be leveraged for identifying tumor margins is fluorescence imaging. Compared to Raman or Photoacoustic imaging, fluorescence imaging suffers from a lower sensitivity on the order of 0.5 nM; however, it could be further improved using multispectral imaging analysis[7]. On a per-molar concentration basis, the MPRs exhibit a higher sensitivity compared to fluorescence agents. However, on a per-mass basis, fluorescent dyes may show better sensitivity than Raman imaging, partially due to the relatively large size of the MPRs.

Nanoparticles also carry some unique advantages such as a very high EPR effect (i.e., accumulation in tumors) compared to small fluorescent dyes.

High grade gliomas, particularly WHO Grade IV glioma (glioblastoma multiforme), are characteristically diffuse, grossly hemorrhagic and necrotic. Therefore, establishing a correspondence between pre-operative and intra-operative tumor delineation represents a significant challenge in neuro-oncology and is one that may be overcome with a multimodal imaging agent such as the one described here. A second significant difficulty in tumor resection is the frequent poor definition of the tumor margin, caused by finger-like protrusions of tumor into the adjacent brain parenchyma. Thus, invasive cells may be found to follow small blood vessels (perivascular cuffing), and in myelinated fiber tracts in which cells show intrafascicular, perifascicular, and interfibrillary migration. The detection of such small tumor extensions requires the highest possible sensitivity and resolution. While most studies examining the effect of intra-operative image guidance on survival used MRI and found an associated improved survival due to the more complete resection[8,9], the resolution of clinical MRI does not resolve such small structures. This could represent a reason why the majority of studies using currently available intra-operative imaging methods report a significant increase in length of survival, but are still not able to achieve long-term survival in high-grade gliomas. In our study we have observed that such finger-like protrusions were also detectable by Raman imaging, indicating that this approach may allow more complete resection in these critical areas. Although we have demonstrated the feasibility of the MPR approach in both the U87MG model as well as in an infiltrating human primary xenograft model, a caveat remains that neither of these two models completely recapitulate human brain tumor pathology and thus eventual clinical studies will be needed for further validation.

C. Supplementary Methods

MRI—Additional Details

For phantom experiments, 50 µL of serial MPR dilutions in MES buffer were placed in customized 384 well plates. For in vivo experiments, animals were first anesthetized in a knockdown box with 3% isoflurane. The animals were then placed on a custom-designed MRI-compatible cradle in a 3 cm inner diameter in house quadrature birdcage radio frequency transmit/receive coil and the tube was connected to a ventilator with 1.3-1.5% isoflurane. A fiber-optic temperature probe and respiratory sensor were placed adjacent to the abdomen of the animal. The coil with the animal was inserted to the iso-center of the magnet. Heated air was pumped into the bore to maintain the body temperature of the animals at physiological levels (34-38°C.).

For quantification of tumor enhancement on MRI, the contrast-to-noise ratio (CNR) was used[10]. An axial slice through the middle of the tumor was chosen in the software Osirix. On this slice, an ROI was drawn outlining the margins of the tumor. A second ROI of the same size was placed over brain tissue of the contralateral hemisphere, which did not contain visible tumor. A third ROI was placed outside of the skin near the skull to record image noise. The CNR was then calculated using the following formula: (signal$_{tumor}$−signal$_{normal\ brain}$)/standard deviation of noise[10].

Raman Imaging—Additional Details

For Raman microscopy, frozen sections were placed on quartz slides (Ted Pella, Inc.) and air-dried. A greater slice thickness (50 µm or 500 µm, depending on the purpose of the experiment) than for immunohistochemistry was chosen in order to increase Raman signal intensity. A 5× or 12× lens was used, and Raman spectral maps and correlating white light images were acquired using the Renishaw Streamline™ function. Spectra were analyzed by least squares analysis using Wire 2.0 Software (Renishaw).

Photoacoustic Imaging—Additional Details

A precision xyz-stage (U500, Aerotech Inc.) with a minimum step size of 1 µm was used to move the transducer and the fiber ring along a planar 2D trajectory. At every position, the acquired signal was averaged over 2 to 4 laser pulses. The time of arrival and the intensity of the laser pulses were recorded using a silicon photodiode (DET10A, Thorlabs). This information was used to synchronize the acquisition and compensate for pulse-to-pulse variations in laser intensity. The analog Photoacoustic signals were amplified using a 30 dB preamplifier (5676/115VAC, Panametrics-Olympus NDT) and digitized using an oscilloscope (Infiniium 54825A, Agilent). The Photoacoustic and ultrasound images were reconstructed as follows: the a-scan from each position of the transducer was band pass filtered with 100% fractional bandwidth, compensated for laser intensity variations and envelope detected. The a-scans were then combined to reconstruct a 3D intensity image of the target. No further post-processing was done on the images. The ultrasound images were acquired using a 5 or 25 MHz transducer.

Photoacoustic-MRI and Raman-MRI co-registration and 3D visualization

Since the Photoacoustic image is intrinsically three-dimensional, we co-registered it to the MRI image and rendered their overlay in 3D. A conventional ultrasound image was taken with the same transducer that was used to acquire the Photoacoustic image, thereby producing perfectly co-registered Photoacoustic and ultrasound images. The ultrasound image highlighted the mouse brain anatomy such as skull curvature, which then allowed us to manually find the exact rigid-body alignment needed to register the ultrasound image to the MRI image. We then applied the same rigid-body alignment to the Photoacoustic image. The 3D rendering of the two images was done in the commercial software Amira™ (Visage Imaging, Inc.). The Raman images were acquired using precise topographical landmarks of the mouse anatomy. The Raman image with its known dimensions and matrix size and the MRI data were then manually co-registered based on these landmarks and the known size and position of the acquired images.

Histology

Brain tissue was embedded in optimal cutting temperature material (O.C.T.; Sakura) and snap-frozen in liquid nitrogen. Frozen sections (10 µm slice thickness) were obtained using a cryotome (Leica). For Raman microscopy, 50 µm or 500 µm sections were cut immediately adjacent to a slice used for immunohistochemistry.

Slides were air-dried for 2 h at RT, then fixed in cold acetone for 5 min and air dried for 1 h. Slides were then washed for 5 min in PBS to remove the O.C.T. Samples were then stained with Rat anti-CD11b (BD Pharmingen, dilution 1:100) for 2 h at RT, Goat anti-Rat-biotinylated (Jackson ImmunoResearch, dilution 1:500) for 30 min at RT, StreptAvidin-AlexaFluor 594 (Invitrogen, dilution 1:300) for 30 min at RT, and Rabbit anti-GFP-AlexaFluor 488 (Invitrogen, dilution 1:500) for 1 h at RT. Slides were counterstained with DAPI for 3 min.

For Olig-2/CD68 double staining, sections were air-dried for 2 h at RT, then fixed in 4% paraformaldehyde in PBS for 10 min and rehydrated by an ethanol gradient wash. After two washes in PBS and permeabilization in 0.3% Triton in PBS for 30 min, sections were incubated in PBS containing 2% BSA, 5% NDS, 0.1% Triton for 1 h at RT, followed by anti-CD68 (1:1000; Serotec) over night at 4° C. After 3 washes with PBS/0.1% Triton sections were incubated with Alexa Fluor 488 donkey anti-rat IgG (H+L) (Invitrogen, dilution 1:500) for 1 h at RT. After washes in PBS/0.1% Triton and blocking in PBS containing 2% BSA, 5% NDS, 0.1% Triton for 20 min at RT, the sections were incubated for 2 h at RT with anti-Olig2 (1:250, Chemicon #9610) followed by PBS/0.1% Triton washes and after 3 washes with PBS/0.1% Triton sections were incubated with Alexa Fluor 555 donkey anti-rabbit IgG (H+L) (Invitrogen, dilution 1:500). After secondary antibody staining, sections were washed with PBS/0.1% Triton and counterstained with DAPI. Samples were examined using a TCS SP2 AOBS (Leica) Confocal Laser Scanning Microscope or DMI6000 inverted fluorescence microscope (Leica).

Statistical Methods

Correlation of signal increase with increasing concentration in vitro was tested with mixed effects linear regression of $\log_{10}$ signal ratio to baseline on $\log_{10}$ concentration, imaging method, and their interaction, with individual phantom area as the random factor. Correlation of signal increase with increasing concentration in living mice, and differences in rate of signal increase between imaging methods in living mice were tested with mixed effects linear regression of $\log_{10}$ signal ratio to baseline on $\log_{10}$ concentration, imaging method, and their interaction, with mouse as the random factor. The MPR tumor targeting experiments were analyzed via one-sided t-test, where MRI and Photoacoustic post-injection measurements were compared against a ratio of 1 with a one-sided one-sample t-test, and Raman post-injection measurements were compared against an average noise value of 0.001 with a one-sided one-sample t-test. The MPR tumor targeting kinetics study initial increase was tested with one-sided student's t-test. The signals were then re-expressed as log of ratio to pre-injection baseline. Differences between imaging methods in time course of signal from 30-120 min were tested with mixed effects linear regression of $\log_{10}$ signal ratio to baseline on $\log_{10}$ concentration, imaging method, and their interaction, with mouse as the random factor.

Mouse Arrangement in the Photoacoustic System

Female nude mice were used for all the Photoacoustic studies. The mice that were scanned in the Photoacoustic system were fully anesthetized using isoflurane delivered through a nose-cone. Prior to the Photoacoustic scan, the head of the mouse was slightly tilted to expose the right lobe to the imaging system. The head was then covered by Gonak gel (Akorn) and covered by a saran-wrap water bath. The ultrasonic transducer in the water bath was therefore acoustically coupled to the mouse brain tissues. This setup allowed the ultrasonic transducer to move freely in 3D while applying only minimal physical pressure on the mouse head (FIG. 16).

Stereotactic Brain Tumor Implantation

All aspects of experimental manipulation were in strict accord with guidelines from the National Institute of Health and have been approved by members of the Stanford Institutional Animal Care and Use Committee (IACUC). Ten week old female nude mice (Charles River), or five week old male SCID mice (Taconic Farms, Inc.), respectively, were anesthetized using 2.0% isoflurane and positioned in a Benchmark® (Leica) stereotactic instrument (FIG. 1.22).

Mice also received a subcutaneous injection of 0.1 mL of a 1:10 dilution of 0.3 mg/mL buprenorphine as additional anesthesia. The top of the animal's head was cleaned with 70% ethanol and betadine. Ophthalmic ointment was applied, a linear skin incision was made over the bregma, and 3% hydrogen peroxide was applied to the periost with a cotton swab. A 27G needle was then used to drill a burrhole into the skull 0.5 mm anterior and 2 mm lateral to the bregma. A 10 µL gas-tight syringe (Hamilton) was then used to inject 2 µL of the eGFP+U87MG-cell suspension or TS543 human glioblastoma cells ($3 \times 10^5$ cells in PBS) in the striatum at a depth of 2.5 mm from the dural surface. TS543 is a glioblastoma multiforme cell line derived from a human glioblastoma and propagated as tumor spheres in NeuroCult media (STEMCELL Technologies). The injection was done slowly over 10 min. The burrhole was occluded with glue to prevent leakage of cerebrospinal fluid, and the skin was closed with surgical clips. Animals were used for experiments after 3-5 weeks, when tumors had reached a size of approximately 5 mm diameter as determined by MRI.

Optical and Raman Photobleaching Studies

We tested the optical stability of the MPRs under increasing durations of light exposure (photobleaching). For assessment of photobleaching by the Photoacoustic laser, the sample was continuously exposed over 30 min (532 nm, power density of 8 mJ/cm$^2$, 10 Hz repetition rate) which were the wavelength and power settings used in our animal experiments.

For assessment of photobleaching by the Raman laser, a 20 µL sample of MPRs in MES buffer was placed in a cell-counting slide. The sample was then continuously exposed to the Raman excitation laser (785 nm) and the Raman signal was recorded every 30 seconds.

Signal Linearity Phantom Study

To test the linearity of the Photoacoustic signal as a function of MPR concentration, we used an agarose phantom with no scattering or absorbing additives. MPRs at increasing concentrations were mixed with warm liquid agarose (n=3 samples for each concentration) forming MPR solutions at 0, 1.2, 2.4, 4.9, 9.8, 19, 39, 78, 156, 312, 625 and 1250 pM (additional concentrations for Raman imaging included concentrations of 300 and 610 fM). Inclusions 2-3 mm deep were made in the agarose phantom and ~100 µL of MPR/agarose solution was poured into the well. Upon solidification of the gel, another layer of ~3 mm of liquid agarose was poured on top of the phantom. A complete 532 nm Photoacoustic image of the phantom was acquired with a step size of 0.25 mm. Three-dimensional cylindrical ROIs of the size of the inclusion were used to estimate the Photoacoustic signal from each well. Subsequently, a Raman image of the phantom was acquired using a 1 mm step size and 1 s integration time. The 2D Raman image was analyzed by ROI analysis using ROIs encompassing the inclusions. Finally, a T1-weighted MR image of the phantom was acquired. Due to the large size of the phantom compared to the RF coil used, and in order to preserve homogeneity of the RF fields across the phantom, the phantom was scanned in two parts, which were later combined together into one image. Two-dimensional ROIs encompassing the inclusions were placed on a slice through the middle of the inclusion using Osirix imaging software. The signal intensity expressed in arbitrary units for each of the three modalities represents the mean from each of the triplicate wells.

MPR Detection and Sensitivity in Living Mice

Solutions of MPRs at different concentrations were mixed with matrigel (Matrigel Basement Membrane Matrix, Phenol Red-free, Becton Dickinson) at 1:1 ratio creating MPR solutions at 50, 100, 200, 400, 800 and 1100 pM. The solutions were then injected subcutaneously (50 µL) to the lower back of mice (n=3). After solidification of the matrigel, the back of the mouse was scanned with the MRI, Photoacoustic and Raman imaging systems. The Photoacoustic image was taken with lateral step size of 0.25 mm using a 5 MHz transducer at a wavelength of 532 nm. Following the Photoacoustic scan, an ultrasound image was acquired using the same 5 MHz transducer and the two images were then overlaid one on top of the other using AMIDE software[11]. Quantification of the Photoacoustic signal was done by drawing a 3D ROI over the inclusion volume that was visualized in the ultrasound image. The Raman image was taken with a lateral step size of 750 μm and an integration time of 1 s. ROI analysis was performed on the 2D Raman image using circular ROIs. T1-weighted fast spin echo MR images were obtained with parameters described before (see Methods). 2D ROIs encompassing the inclusions were placed within a slice through the middle of the inclusion using the software Osirix. The signal intensity expressed in arbitrary units for each of the three modalities represents the mean for each of the three mice.

Quantitative Raman Spectral Analysis

The direct classical least squares (DCLS) method was used in this work to perform quantitative analysis of Raman spectroscopy[12,13]. DDLS finds the linear combination of spectra from the MPR Raman signal contained in the area of interest (brain) that most closely matches the Raman spectrum of the MPRs injected intravenously. The pure component spectrum of the MPRs that contains the Raman-active organic molecule, trans-1,2-bis(4-pyridyl)-ethylene, was acquired from a pure 3 mL sample aliquoted onto a quartz slide under the microscope. The multiplicative constants derived by the DCLS analysis are proportional to the concentration of the pure components. Before injection and scanning, a pure spectra component was taken from the MPRs along with the mouse Raman background signal that was used as a background component (which was later subtracted). The DCLS method gave very accurate results since the pure spectral component remained consistent throughout the analysis. The quantitative data shown was analyzed based on the Raman maps acquired from each mouse at various time points. A region of interest was drawn around the tumor area and an average accumulation of nanoparticles was estimated in that region based on the pure spectral component of the MPRs, as described above. For some experiments, such as photobleaching studies, Raman spectra from a single point over the sample of interest were analyzed.

Scanning Transmission Electron Microscopy of Tissue Samples

Tissue samples from both healthy brain and tumor were fixed in a solution of 4% paraformaldehyde in 0.1 M sodium cacodylate buffer. Samples were then stained with 1% osmium tetroxide in water at 4° C. for 2 h. After 2 h, the tissue samples were rinsed with deionized water and stained with 1% uranyl acetate at 4° C. overnight. Samples were then dehydrated in progressively higher concentrations of ethanol at 4° C.; 50%, 70%, and 95%. The tissue samples were then allowed to gradually warm to RT. Samples were further dehydrated 2× in 100% ethanol and 3× in propylene oxide. Samples were then embedded in Embed 812 epoxy resin (EMSdiasum). Samples were placed in 1:1 solution of Embed 812:propylene oxide for 1 h at RT. Samples were then placed in 2:1 solution of Embed 812:propylene oxide overnight. Finally samples were placed in 100% Embed 812 for 1 h before being placed in molds and cured overnight at 60° C. Thin sections (150 nm) were then cut from the tissue samples using an Ultracut S microtome (Leica) and placed on 200 mesh bare copper grids. The sections were examined without coverslip using a Tecnai G2 X-Twin (FEI) scanning transmission electron microscope (STEM) operating at 120 kV in scanning mode.

Scanning Electron Microscopy of Tissue Samples

Images of histology slides of brain tissue stained with hematoxylin and eosin were acquired using a DM 2000 light microscope (Leica). Images were taken and stitched together to create a large composite image of the entire brain section. The histology slides were then coated with a thin AuPd film to improve conductivity and placed in a XHR scanning electron microscope (SEM) (Magellan). The SEM was operated at 15 kV with a probe current of 50 pA. Both secondary electron and backscattered electron images were collected. Backscattered electron imaging was utilized to locate the MPRs in the brain tissue.

Inductively Coupled Plasma Atomic Emission Spectroscopy (ICP-AES)

An aliquot of 3854 of 3.86 nM MPR suspension was washed 2× in water and then pelleted by centrifugation. The pellet was re-suspended in 2 mL of 10 M of sodium hydroxide and sonicated for 10 min in a sonication bath at RT. This was followed by slow addition of 70% $HNO_3$ until the pH became acidic. The volume of the resulted mixture was brought to 10 mL and analyzed for the presence of $Gd^{+3}$ ions using an IRIS Advantage/1000 Radial ICAP Spectrometer (Thermo Scientific).

Tissue-mimicking Phantom for Comparing Depth of Penetration of Photoacoustic Versus Raman Imaging The phantom was based on a 1% agarose mixed with India Ink to mimic tissue absorption (to make the final agarose-solution at optical absorbance of 1.0 $cm^{-1}$) and Liposyn 0.5% to mimic tissue scattering. The agarose liquid was left to solidify in a plastic container that was slightly tilted. As the agarose solidified, small inclusions of ~3 mm diameter and 1-2 mm in depth were made using a small pipette tip. MPRs mixed in liquid agarose-solution at 1 nM concentration were embedded in the small inclusions. As the inclusions solidified, the plastic container was positioned on a flat surface and an additional layer of agarose-solution was poured on the phantom to seal it.

REFERENCES FOR SUPPLEMENTARY INFORMATION, EACH OF WHICH IS INCORPORATED HEREIN BY REFERENCE 1. de la Zerda, A., et al. Carbon nanotubes as photoacoustic molecular imaging agents in living mice. *Nat Nanotechnol* 3, 557-562 (2008).
2. Eghtedari, M., et al. High sensitivity of in vivo detection of gold nanorods using a laser optoacoustic imaging system. *Nano Lett.* 7, 1914-1918 (2007).
3. Razansky, D., et al. Multispectral opto-acoustic tomography of deep-seated fluorescent proteins in vivo. *Nat Photon* 3, 412-417 (2009).
4. Kim, J. W., Galanzha, E. I., Shashkov, E. V., Moon, H. M. & Zharov, V. P. Golden carbon nanotubes as multimodal photoacoustic and photothermal high-contrast molecular agents. *Nat Nanotechnol* 4, 688-694 (2009).
5. Kim, G., et al. Indocyanine-green-embedded PEBBLEs as a contrast agent for photoacoustic imaging. *J. Biomed. Opt.* 12, 044020 (2007).
6. Agarwal, A., et al. Targeted gold nanorod contrast agent for prostate cancer detection by photoacoustic imaging. *J. Appl. Phys.* 102, 064701-064704 (2007).
7. Mansfield, J. R., Gossage, K. W., Hoyt, C. C. & Levenson, R. M. Autofluorescence removal, multiplexing, and automated analysis methods for in-vivo fluorescence imaging. *Journal of biomedical optics* 10, 41207 (2005).
8. Schneider, J. P., et al. Intraoperative MRI to guide the resection of primary supratentorial glioblastoma multiforme—a quantitative radiological analysis. *Neuroradiology* 47, 489-500 (2005).
9. Senft, C., et al. Influence of iMRI-guidance on the extent of resection and survival of patients with glioblastoma multiforme. *Technol Cancer Res Treat* 9, 339-346 (2010).
10. Bushberg, J. T., Seibert., J. A., Leidholdt, E. M. & Boone, J. M. *Essential Physics of Medical Imaging*, (Lippincott Williams & Wilkins, 2001).
11. Loening, A. M. & Gambhir, S. S. AMIDE: a free software tool for multimodality medical image analysis. *Mol. Imaging* 2, 131-137 (2003).
12. Haaland, D. M. & Easterling, R. G. Improved Sensitivity of Infrared Spectroscopy by the Application of Least Squares Methods. *Appl Spec* 34, 539-548 (1980).
13. Pelletier, M. J. Quantitative Analysis Using Raman Spectroscopy. *Appl Spect* 57, 20A-42A (2003).

Example 2

MPR nanoparticles were prepared as previously described in Example 1, and 50 µL of the 4.8 nM lot added to 950 µL of 50% mouse serum or DDI at 37° C. for 2 or 24 hours in triplicate. The MPRs were concentrated by centrifugation and the silica shell dissolved with strong base, neutralized, and diluted to 5 mL with 5% nitric acid. Mole ratios of Gd to MPR were determined as follows (FIG. 2.1). The source NPs contained 79,340±2,270 Gd per NP. At 24 hours incubation with 50% mouse serum this ratio decreased to 68,640±337.

The amount of gadolinium dissociated from MPR and in solvent was also quantified (FIG. 2.2). The percentage of Gd free in solvent (serum or water) was 0.37%, 4.17%, and 6.06% of the starting concentration for 24H water, 24H serum, and 2H serum incubation experiments, respectively.

The amount of gadolinium in equimolar raw SERS NPs or in 500 µL pure mouse serum was also measured. In both cases, two of the three measurements were below the detection limit of the instrument with the remaining value of 1.7 E-9 and 3.6E-10 moles for serum and NPs, respectively.

The loading achieved is unexpectedly higher than that predicted by a size-dependent model of silica:Gd loading (FIG. 2.3). The loading level of 79,000 Gd:NP is 1.5 times higher than that predicted for 120-140 nm silica of 52,000 because MRI agent disposal is influenced by both direct and indirect binding. The porous nature of the silica used here provides a high surface area suitable for the loading of many MRI agents.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A probe, comprising:
a nanoparticle core, a reporter compound layer disposed on the core, a silica shell consisting of polymeric silicon dioxide linking 3-mercaptopropyl-trimethoxysilane (MPTMS) moieties directly attached to the nanoparticle core surrounding the reporter compound layer and the core, and a plurality of MRI-detectable agents disposed on the silica shell; wherein the core is a photoacoustic probe having a detectable photoacoustic signal; wherein the reporter compound is a Raman-active reporter, wherein the interaction of the Raman-active reporter with the core produces a detectable vibrational signal.

2. The probe of claim 1, wherein the core has a shape selected from a spherical shape and a rod shape.

3. The probe of claim 1, wherein the nanoparticle core is a gold nanoparticle core and the MRI agent is Gd.

4. The probe of claim 1, wherein the MRI agent is a plurality of Gd ions, and wherein the Gd ions are directly disposed on the encapsulant surface.

5. The probe of claim 1, wherein the MRI agent is a plurality of Gd ions, and wherein the Gd ions are attached indirectly to the encapsulant surface via a linker.

6. The probe of claim 1, wherein the MRI agent is a plurality of Gd ions, and wherein some of the Gd ions are attached indirectly to the encapsulant surface via a linker and wherein some of the Gd ions are disposed directly on the encapsulant surface.

7. The probe of claim 6, wherein the ratio of the Gd directly disposed on the shell surface and Gd indirectly linked to the encapsulant surface is about 1:10 to 10:1.

8. The probe of claim 1, wherein the Raman-active reporter is selected from: a polycyclic aromatic compound, a heteroaromatic compound, and a combination thereof.

9. The probe of claim 1, wherein the nanoparticle core is selected from: gold, silver, and a combination thereof.

10. The probe of claim 1, wherein the shell is composed of at least one of silica, a metallic film different from the core material, a polymer, and a polymeric chelator.

11. The probe of claim 1, wherein the MRI agent is selected from: Gd, iron oxide, a paramagnetic CEST agent, and a combination thereof.

12. The probe of claim 1, wherein the probe has a diameter of about 100 to 160 nm.

13. A method of imaging a brain tumor, comprising the steps of:
(a) delivering to a subject human or animal a composition comprising a multimodal nanoprobe, said multimodal nanoprobe comprising a nanoparticle core, a reporter compound layer disposed on the core, a silica shell consisting of polymeric silicon dioxide linking 3-mercaptopropyl-trimethoxysilane (MPTMS) moieties directly attached to the nanoparticle core surrounding the reporter compound layer and the core, and a plurality of MRI-detectable agents disposed on the silica shell; wherein the core is a photoacoustic probe having a detectable photoacoustic signal; wherein the reporter compound is a Raman-active reporter, wherein the interaction of the Raman-active reporter with the core produces a detectable vibrational signal;

(b) preoperatively obtaining a MRI signal from the multimodal nanoprobe in the tumorous tissue within the brain of the subject human or animal and generating from the MRI signal a first image, wherein the first image indicates a location of tumorous brain tissue and a macroscopic delineation thereof within the brain of the subject human or animal;

(c) intra-operatively obtaining a deep tissue penetration photoacoustic signal from the multimodal nanoprobe in the tumorous tissue within the brain of the subject human or animal and generating from the photoacoustic signal a second image, wherein the second image indicates the location of tumorous brain tissue within the brain of the subject human or animal;

(d) intra-operatively obtaining a Raman vibrational signal from the multimodal nanoprobe in the tumorous tissue within the brain of the subject human or animal and generating from the Raman vibrational signal a third image, wherein the third image indicates the margin of tumorous brain tissue within the brain of the subject human or animal; and (e) intra-operatively overlaying at least two of the first, the second, and the third images with an MR image of the brain of the subject human or animal to generate an overlay image of the tumorous brain tissue within the brain of the subject human or animal by and determining from said overlay image at least one of the location and the margin of the tumorous brain tissue within the brain of the subject human or animal.

14. The method of claim 13, wherein the nanoparticle core has a shape selected from a spherical shape and a rod shape.

15. The method of claim 13, wherein the nanoparticle core is a gold nanoparticle core and the MRI agent is Gd.

16. The method of claim 13, wherein the MRI agent is a plurality of Gd ions, and wherein the Gd ions are directly disposed on the encapsulant surface.

17. The method of claim 13, wherein the MRI agent is a plurality of Gd ions, and wherein the Gd ions are attached indirectly to the encapsulant surface via a linker.

18. The method of claim 13, wherein the MRI agent is a plurality of Gd ions, and wherein some of the Gd ions are attached indirectly to the encapsulant surface via a linker and wherein some of the Gd ions are disposed directly on the encapsulant surface.

19. The method of claim 18, wherein the ratio of the Gd directly disposed on the shell surface and Gd indirectly linked to the encapsulant surface is about 1:10 to 10:1.

20. The method of claim 13, wherein the Raman-active reporter is selected from: a polycyclic aromatic compound, a heteroaromatic compound, and a combination thereof.

21. The method of claim 13, wherein the nanoparticle core is selected from: gold, silver, and a combination thereof.

22. The method of claim 13, wherein the shell is composed of at least one of silica, a metallic film different from the core material, a polymer, and a polymeric chelator.

23. The method of claim 13, wherein the MRI agent is selected from: Gd, iron oxide, a paramagnetic CEST agent, and a combination thereof.

24. The method of claim 13, wherein the probe has a diameter of about 100 to 160 nm.

* * * * *